United States Patent
Carr et al.

(10) Patent No.: US 6,495,344 B1
(45) Date of Patent: *Dec. 17, 2002

(54) PHENYLALANINE-FREE PROTEIN AND DNA CODING THEREFOR

(75) Inventors: Noel Gordon Carr; Nicholas Harold Mann, both of Warwickshire (GB)

(73) Assignee: Pharming Holding N. V. (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 182 days.

(21) Appl. No.: 08/545,573

(22) PCT Filed: May 16, 1994

(86) PCT No.: PCT/GB94/01046

§ 371 (c)(1),
(2), (4) Date: Jan. 16, 1996

(87) PCT Pub. No.: WO94/28126

PCT Pub. Date: Dec. 8, 1994

(30) Foreign Application Priority Data

May 20, 1993 (GB) ............................................ 9310472

(51) Int. Cl.$^7$ .................. C12P 21/06; C07H 21/04; A61K 35/78; A01N 37/18
(52) U.S. Cl. ............... 435/69.1; 435/320.1; 435/252.3; 435/252.33; 435/254.21; 536/23.1; 536/23.5; 530/350; 530/360; 530/367; 514/2
(58) Field of Search .................. 536/23.1, 23.5; 435/320.1, 252.3, 252.33, 252.35, 254.21, 69.1; 530/350, 360, 367; 514/2

(56) References Cited

U.S. PATENT DOCUMENTS

| | | | |
|---|---|---|---|
| 4,016,147 A | 4/1977 | Fujimaki et al. | ............ 260/112 |
| 4,371,466 A | 2/1983 | McGregor | ............... 260/112.5 |
| 4,474,761 A | 10/1984 | Caen et al. | ................. 424/177 |
| 6,004,930 A | * 12/1999 | Hainline | ...................... 514/12 |

FOREIGN PATENT DOCUMENTS

| | | |
|---|---|---|
| GB | 2 068 971 A | 1/1980 |
| GB | 2 068 969 A | 2/1989 |
| WO | WO 93/04171 | 3/1993 |

OTHER PUBLICATIONS

Biernatt [I] et al. (1987) The construction and cloning of synthetic genes coding for artificial proteins and expression studies to obtain fusion proteins. Protein Engineering. 1/4:345–351.*

Biernat [ii] et al. (1987) Expression of synthetic genes coding for completely new, nutritionally rich, artificial proteins. Protein Engineering 1/4:353–358.*

Watanabe et al. (1988) Construction of a Bioreactor with Immobilized Yeast Cells for Production of a Low–Phenylalanine Peptide Mixture as a Phenylketonuria Foodstuff. Agric. Biol. Chem. vol. 52, No. 12, pp. 2989–2994.*

McKnight et al. (1989) Cloning and Sequencing of a Complementary Deoxribonucleic Acid Coding for a Bovine alpha–s1–Casein A from Mammary Tissue of a Homozygous B Variant Cow. J. Dairy Sci. vol. 72, pp. 2464–2473.*

Nisbet et al. (1981) The Complete Amino–Acid Sequence of Hen Ovalbumin. Eur. J. Biochem. vol. 115, pp. 335–345.*

Greene et al. (1993) Changes in Global Stability and Local Structure of Cytochrome c Upon Substituting Phenylalanine–82 with Tyrosine. J. Inorg. Biochem. vol. 51, pp. 663–676.*

Kunkel (1985) Rapid and Efficient Site–Specific Mutagenesis Without Phenotypic Selection. vol. 82, pp. 488–492.*

Romanos (1992) Foreign Gene Expression in Yeast: a Review. Yeast. vol. 8, pp. 423–488.*

"Cloning and Sequencing of a Complementary Deoxyribonucleic Acid Coding for a Bovine $_{\alpha s1}$–Casein A from Mammary Tissue of a Homozygous B Variant Cow," McKnight, Robert, et al., *Journal of Dairy Science*, vol. 72, No. 10, 1989.

"Genetic Engineering of the Caseins to Modify the Behavior of Milk During Processing: A Review," Jimenez–Flores, Rafael, et al., *Journal of Dairy Science*, vol. 71, No. 10, 1988.

"Preparation Of A Low Phenylalanine Protein By Enzymatic Process," Monckeberg, A., et al., *Research in Food Science and Nutrition*, vol. 3, 1983.

* cited by examiner

Primary Examiner—Karen Cochrane Carlson
Assistant Examiner—Rita Mitra
(74) Attorney, Agent, or Firm—Townsend and Townsend and Crew LLP

(57) ABSTRACT

A DNA molecule coding for a food protein, such as ovalbumin or casein, modified so that the codons for phenylalanine have been omitted or replaced by codons for one or more other metabolisable amino acids. Also a modified edible protein coded for by such a DNA molecule. Such modified proteins are useful in the nutrition of patients suffering from phenylketonuria.

15 Claims, 23 Drawing Sheets

```
gacatacagc tagaaagctg tattgccttt agcactcaag ctcaaaagac aactcagagt   60
tcaccatggg ctccatcggc gcagcaagca tggaattttg ttttgatgta ttcaaggagc  120
tcaaagtcca ccatgccaat gagaacatct tctactgccc cattgccatc atgtcagctc  180
tagccatggt atacctgggt gcaaaagaca gcaccaggac acagataaat aaggttgttc  240
gctttgataa acttccagga ttcggagaca gtattgaagc tcagtgtggc acatctgtaa  300
acgttcactc ttcacttaga gacatcctca accaaatcac caaaccaaat gatgtttatt  360
cgttcagcct tgccagtaga ctttatgctg aagagagata cccaatcctg ccagaatact  420
tgcagtgtgt gaaggaactg tatagaggag cttggaacc tatcaacttt caaacagctg  480
cagatcaagc cagagagctc atcaattcct gggtagaaag tcagacaaat ggaattatca  540
gaaatgtcct tcagccaagc tccgtggatt ctcaaactgc aatggttctg gttaatgcca  600
ttgtcttcaa aggactgtgg gagaaaacat ttaaggatga agacacacaa gcaatgcctt  660
tcagagtgac tgagcaagaa agcaaacctg tgcagatgat gtaccagatt ggtttattta  720
gagtggcatc aatggcttct gagaaatga agatcctgga gcttccattt gccagtggga  780
caatgagcat gttggtgctg ttgcctgatg aagtctcagg ccttgagcag cttgagagta  840
taatcaactt tgaaaaactg actgaatgga ccagttctaa tgttatggaa gagaggaaga  900
tcaaagtgta cttacctcgc atgaagatgg aggaaaaata caacctcaca tctgtcttaa  960
tggctatggg cattactgac gtgtttagct cttcagccaa tctgtctggc atctcctcag 1020
cagagagcct gaagatatct caagctgtcc atgcagcaca tgcagaaatc aatgaagcag 1080
gcagagaggt ggtagggtca gcagaggctg gagtggatgc tgcaagcgtc tctgaagaat 1140
ttagggctga ccatccattc ctcttctgta tcaagcacat cgcaaccaac gccgttctct 1200
tctttggcag atgtgtttcc ccttaaaaag aagaaagctg aaaaactctg tcccttccaa 1260
caagacccag agcactgtag tatcagggt aaaatgaaaa gtatgttctc tgctgcatcc 1320
agacttcata aaagctggag cttaatctag aaaaaaaatc agaaagaaat tacactgtga 1380
gaacaggtgc aattcacttt tcctttacac agagtaatac tggtaactca tggatgaagg 1440
cttaagggaa tgaaattgga ctcacagtac tgagtcatca cactgaaaaa tgcaacctga 1500
tacatcagca gaaggtttat gggggaaaaa tgcagccttc caattaagcc agatatctgt 1560
atgaccaagc tgctccagaa ttagtcactc aaaatctctc agattaaatt atcaactgtc 1620
accaaccatt cctatgctga caaggcaatt gcttgttctc tgtgttcctg atactacaag 1680
gctcttcctg acttcctaaa gatgcattat aaaaatctta taattcacat ttctccctaa 1740
actttgactc aatcatggta tgttggcaaa tatggtatat tactattcaa attgttttcc 1800
ttgtacccat atgtaatggg tcttgtgaat gtgctctttt gttcctttaa tcataataaa 1860
aacatgttta agc                                                   1873
```

FIG. 1

| | | | | | |
|---|---|---|---|---|---|
| 1 | MGSIGAASME | FCFDVFKELK | VHHANENIFY | CPIAIMSALA | MVYLGAKDST |
| 51 | RTQINKVVRF | DKLPGFGDSI | EAQCGTSVNV | HSSLRDILNQ | ITKPNDVYSF |
| 101 | SLASRLYAEE | RYPILPEYLQ | CVKELYRGGL | EPINFQTAAD | QARELINSWV |
| 151 | ESQTNGIIRN | VLQPSSVDSQ | TAMVLVNAIV | FKGLWEKTFK | DEDTQAMPFR |
| 201 | VTEQESKPVQ | MMYQIGLFRV | ASMASEKMKI | LELPFASGTM | SMLVLLPDEV |
| 251 | SGLEQLESII | NFEKLTEWTS | SNVMEERKIK | VYLPRMKMEE | KYNLTSVLMA |
| 301 | MGITDVFSSS | ANLSGISSAE | SLKISQAVHA | AHAEINEAGR | EVVGSAEAGV |
| 351 | DAASVSEEFR | ADHPFLFCIK | HIATNAVLFF | GRCVSP | |

FIG. 2

| | | | | | |
|---|---|---|---|---|---|
| 1 | MGSIGAASME | CDVKELKVHH | ANENIYCPIA | IMSALAMVYL | GAKDSTRTQI |
| 51 | NKVVRDKLPG | GDSIEAQCGT | SVNVHSSLRD | ILNQITKPND | VYSSLASRLY |
| 101 | AEERYPILPE | YLQCVKELYR | GGLEPINQTA | ADQARELINS | WVESQTNGII |
| 151 | RNVLQPSSVD | SQTAMVLVNA | IVKGLWEKTK | DEDTQAMPRV | TEQESKPVQM |
| 201 | MYQIGLRVAS | MASEKMKILE | LPASGTMSML | VLLPDEVSGL | EQLESIINEK |
| 251 | LTEWTSSNVM | EERKIKVYLP | RMKMEEKYNL | TSVLMAMGIT | DVSSSANLSG |
| 301 | ISSAESLKIS | QAVHAAHAEI | NEAGREVVGS | AEAGVDAASV | SEERADHPLC |
| 351 | IKHIATNAVL | GRCVSP | | | |

FIG. 3

| | | | | | |
|---|---|---|---|---|---|
| 1 | MGSIGAASME | YCYDVYKELK | VHHANENIYY | CPIAIMSALA | MVYLGAKDST |
| 51 | RTQINKVVRY | DKLPGYGDSI | EAQCGTSVNV | HSSLRDILNQ | ITKPNDVYSY |
| 101 | SLASRLYAEE | RYPILPEYLQ | CVKELYRGGL | EPINYQTAAD | QARELINSWV |
| 151 | ESQTNGIIRN | VLQPSSVDSQ | TAMVLVNAIV | YKGLWEKTYK | DEDTQAMPYR |
| 201 | VTEQESKPVQ | MMYQIGLYRV | ASMASEKMKI | LELPYASGTM | SMLVLLPDEV |
| 251 | SGLEQLESII | NYEKLTEWTS | SNVMEERKIK | VYLPRMKMEE | KYNLTSVLMA |
| 301 | MGITDVYSSS | ANLSGISSAE | SLKISQAVHA | AHAEINEAGR | EVVGSAEAGV |
| 351 | DAASVSEEYR | ADHPYLYCIK | HIATNAVLYY | GRCVSP | |

FIG. 4

```
ATGGGTTCTA TTGGTGCTGC TTCTATGGAA TGTGATGTTA AAGAATTGAA AGTTCATCAT   60

GCTAATGAAA ATATTTATTG TCCAATTGCT ATTATGTCTG CTTTGGCTAT GGTTTATTTG  120

GGTGCTAAAG ATTCTACTAG AACTCAAATT AATAAAGTTG TTAGAGATAA ATTGCCAGGT  180

GGTGATTCTA TTGAAGCTCA ATGTGGTACT TCTGTTAATG TTCATTCTTC TTTGAGAGAT  240

ATTTTGAATC AAATTACTAA ACCAAATGAT GTTTATTCTT CTTTGGCTTC TAGATTGTAT  300

GCTGAAGAAA GATATCCAAT TTTGCCAGAA TATTTGCAAT GTGTTAAAGA ATTGTATAGA  360

GGTGGTTTGG AACCAATTAA TCAAACTGCT GCTGATCAAG CTAGAGAATT GATTAATTCT  420

TGGGTTGAAT CTCAAACTAA TGGTATTATT AGAAATGTTT TGCAACCATC TTCTGTTGAT  480

TCTCAAACTG CTATGGTTTT GGTTAATGCT ATTGTTAAAG GTTTGTGGGA AAAAACTAAA  540

GATGAAGATA CTCAAGCTAT GCCAAGAGTT ACTGAACAAG AATCTAAACC AGTTCAAATG  600

ATGTATCAAA TTGGTTTGAG AGTTGCTTCT ATGGCTTCTG AAAAAATGAA AATTTTGGAA  660

TTGCCAGCTT CTGGTACTAT GTCTATGTTG GTTTTGTTGC AGATGAAGT TTCTGGTTTG  720

GAACAATTGG AATCTATTAT TAATGAAAAA TTGACTGAAT GGACTTCTTC TAATGTTATG  780

GAAGAAAGAA AAATTAAAGT TTATTTGCCA AGAATGAAAA TGGAAGAAAA ATATAATTTG  840

ACTTCTGTTT TGATGGCTAT GGGTATTACT GATGTTTCTT CTTCTGCTAA TTTGTCTGGT  900

ATTTCTTCTG CTGAATCTTT GAAAATTTCT CAAGCTGTTC ATGCTGCTCA TGCTGAAATT  960

AATGAAGCTG GTAGAGAAGT TGTTGGTTCT GCTGAAGCTG TGTTGATGC TGCTTCTGTT 1020

TCTGAAGAAA GAGCTGATCA TCCATTGTGT ATTAAACATA TTGCTACTAA TGCTGTTTTG 1080

GGTAGATGTG TTTCTCCA                                                1098
```

FIG. 5

```
ATGGGTTCTA TTGGTGCTGC TTCTATGGAA TATTGTTATG ATGTTTATAA AGAATTGAAA    60
GTTCATCATG CTAATGAAAA TATTTATTAT TGTCCAATTG CTATTATGTC TGCTTTGGCT   120
ATGGTTTATT TGGGTGCTAA AGATTCTACT AGAACTCAAA TTAATAAAGT TGTTAGATAT   180
GATAAATTGC CAGGTTATGG TGATTCTATT GAAGCTCAAT GTGGTACTTC TGTTAATGTT   240
CATTCTTCTT TGAGAGATAT TTTGAATCAA ATTACTAAAC AAATGATGT TTATTCTTAT   300
TCTTTGGCTT CTAGATTGTA TGCTGAAGAA AGATATCCAA TTTTGCCAGA ATATTTGCAA   360
TGTGTTAAAG AATTGTATAG AGGTGGTTTG GAACCAATTA ATTATCAAAC TGCTGCTGAT   420
CAAGCTAGAG AATTGATTAA TTCTTGGGTT GAATCTCAAA CTAATGGTAT TATTAGAAAT   480
GTTTTGCAAC CATCTTCTGT TGATTCTCAA ACTGCTATGG TTTTGGTTAA TGCTATTGTT   540
TATAAAGGTT TGTGGGAAAA AACTTATAAA GATGAAGATA CTCAAGCTAT GCCATATAGA   600
GTTACTGAAC AAGAATCTAA ACCAGTTCAA ATGATGTATC AAATTGGTTT GTATAGAGTT   660
GCTTCTATGG CTTCTGAAAA AATGAAAATT TTGGAATTGC CATATGCTTC TGGTACTATG   720
TCTATGTTGG TTTTGTTGCC AGATGAAGTT TCTGGTTTGG AACAATTGGA ATCTATTATT   780
AATTATGAAA AATTGACTGA ATGGACTTCT TCTAATGTTA TGGAAGAAAG AAAAATTAAA   840
GTTTATTTGC CAAGAATGAA AATGGAAGAA AAATATAATT TGACTTCTGT TTTGATGGCT   900
ATGGGTATTA CTGATGTTTA TTCTTCTTCT GCTAATTTGT CTGGTATTTC TTCTGCTGAA   960
TCTTTGAAAA TTTCTCAAGC TGTTCATGCT GCTCATGCTG AAATTAATGA AGCTGGTAGA  1020
GAAGTTGTTG GTTCTGCTGA AGCTGGTGTT GATGCTGCTT CTGTTTCTGA AGAATATAGA  1080
GCTGATCATC CATATTTGTA TTGTATTAAA CATATTGCTA CTAATGCTGT TTTGTATTAT  1140
GGTAGATGTG TTTCTCCA                                                1158
```

FIG. 6

```
CTGCAGGATC CCGGGAATTC AAGCTTATGG GTTCTATTGG TGCTGCTTCT ATGGAATGTG   60
ATGTTAAAGA ATTGAAAGTT CATCATGCTA ATGAAAATAT TTATTGTCCA ATTGCTATTA  120
TGTCTGCTTT GGCTATGGTT TATTTGGGTG CTAAAGATTC TACTAGAACT CAAATTAATA  180
AAGTTGTTAG AGATAAATTG CCAGGTGGTG ATTCTATTGA AGCTCAATGT GGTACTTCTG  240
TTAATGTTCA TTCTTCTTTG AGAGATATTT TGAATCAAAT TACTAAACCA AATGATGTTT  300
ATTCTTCTTT GGCTTCTAGA TTGTATGCTG AAGAAAGATA TCCAATTTTG CCAGAATATT  360
TGCAATGTGT TAAAGAATTG TATAGAGGTG GTTTGGAACC AATTAATCAA ACTGCTGCTG  420
ATCAAGCTAG AGAATTGATT AATTCTTGGG TTGAATCTCA AACTAATGGT ATTATTAGAA  480
ATGTTTTGCA ACCATCTTCT GTTGATTCTC AAACTGCTAT GGTTTTGGTT AATGCTATTG  540
TTAAAGGTTT GTGGGAAAAA ACTAAAGATG AAGATACTCA AGCTATGCCA AGAGTTACTG  600
AACAAGAATC TAAACCAGTT CAAATGATGT ATCAAATTGG TTTGAGAGTT GCTTCTATGG  660
CTTCTGAAAA AATGAAAATT TTGGAATTGC CAGCTTCTGG TACTATGTCT ATGTTGGTTT  720
GTTGCCAGA TGAAGTTTCT GGTTTGGAAC AATTGGAATC TATTATTAAT GAAAAATTGA  780
CTGAATGGAC TTCTTCTAAT GTTATGGAAG AAAGAAAAAT TAAAGTTTAT TTGCCAAGAA  840
TGAAAATGGA AGAAAAATAT AATTTGACTT CTGTTTTGAT GGCTATGGGT ATTACTGATG  900
TTTCTTCTTC TGCTAATTTG TCTGGTATTT CTTCTGCTGA ATCTTTGAAA ATTTCTCAAG  960
CTGTTCATGC TGCTCATGCT GAAATTAATG AAGCTGGTAG AGAAGTTGTT GGTTCTGCTG 1020
AAGCTGGTGT TGATGCTGCT TCTGTTTCTG AAGAAAGAGC TGATCATCCA TTGTGTATTA 1080
AACATATTGC TACTAATGCT GTTTGGGTA GATGTGTTTC TCCATAATAA AAAGAAGAAA 1140
GCTGAAAAAC TCTGTCCCTT CCAACAAGAC CCAGAGCACT GTAGTATCAG GGGTAAAATG 1200
AAAAGTATGT TCTCTGCTGC ATCCAGACTT CATAAAAGCT GGAGCTTAAT CTAGAAAAAA 1260
AATCAGAAAG AAATTACACT GTGAGAACAG GTGCAATTCA CTTTTCCTTT ACACAGAGTA 1320
ATACTGGTAA CTCATGGATG AAGGCTTAAG GGAATGAAAT TGGACTCACA GTACTGAGTC 1380
ATCACACTGA AAAATGCAAC CTGATACATC AGCAGAAGGT TTATGGGGA AAAATGCAGC 1440
CTTCCAATTA AGCCAGATAT CTGTATGACC AAGCTGCTCC AGAATTAGTC ACTCAAAATC 1500
TCTCAGATTA AATTATCAAC TGTCACCAAC CATTCCTATG CTGACAAGGC AATTGCTTGT 1560
TCTCTGTGTT CCTGATACTA CAAGGCTCTT CCTGACTTCC TAAAGATGCA TTATAAAAAT 1620
CTTATAATTC ACATTTCTCC CTAAACTTTG ACTCAATCAT GGTATGTTGG CAAATATGGT 1680
ATATTACTAT TCAAATTGTT TTCCTTGTAC CCATATGTAA TGGGTCTTGT GAATGTGCTC 1740
TTTTGTTCCT TTAATCATAA TAAAAACATG TTTAAGCCTG CAGGATCCCG GGAATTCAAG 1800
CTT                                                              1803
```

FIG. 7

```
5'CTGCAGGATC CCGGGAATTC AAGCTTATGC ATCATCATCA TCATCATGGT TCTATTGGTG  60
  CTGCTTCTAT GGAATGTGAT GTTAAAGAAT TGAAAGTTCA TCATGCTAAT GAAAATATTT 120
  ATTGTCCAAT TGCTATTATG TCTGCTTTGG CTATGGTTTA TTTGGGTGCT AAAGATTCTA 180
  CTAGAACTCA AATTAATAAA GTTGTTAGAG ATAAATTGCC AGGTGGTGAT TCTATTGAAG 240
  CTCAATGTGG TACTTCTGTT AATGTTCATT CTTCTTTGAG AGATATTTTG AATCAAATTA 300
  CTAAACCAAA TGATGTTTAT TCTTCTTTGG CTTCTAGATT GTATGCTGAA GAAAGATATC 360
  CAATTTTGCC AGAATATTTG CAATGTGTTA AGAATTGTA TAGAGGTGGT TTGGAACCAA 420
  TTAATCAAAC TGCTGCTGAT CAAGCTAGAG AATTGATTAA TTCTTGGGTT GAATCTCAAA 480
  CTAATGGTAT TATTAGAAAT GTTTTGCAAC CATCTTCTGT TGATTCTCAA ACTGCTATGG 540
  TTTTGGTTAA TGCTATTGTT AAAGGTTTGT GGGAAAAAAC TAAAGATGAA GATACTCAAG 600
  CTATGCCAAG AGTTACTGAA CAAGAATCTA AACCAGTTCA AATGATGTAT CAAATTGGTT 660
  TGAGAGTTGC TTCTATGGCT TCTGAAAAAA TGAAAATTTT GGAATTGCCA GCTTCTGGTA 720
  CTATGTCTAT GTTGGTTTTG TTGCCAGATG AAGTTTCTGG TTTGGAACAA TTGGAATCTA 780
  TTATTAATGA AAAATTGACT GAATGGACTT CTTCTAATGT TATGGAAGAA AGAAAAATTA 840
  AGTTTATTT GCCAAGAATG AAAATGGAAG AAAAATATAA TTTGACTTCT GTTTGATGG 900
  CTATGGGTAT TACTGATGTT TCTTCTTCTG CTAATTTGTC TGGTATTTCT TCTGCTGAAT 960
  CTTTGAAAAT TTCTCAAGCT GTTCATGCTG CTCATGCTGA AATTAATGAA GCTGGTAGAG 1020
  AAGTTGTTGG TTCTGCTGAA GCTGGTGTTG ATGCTGCTTC TGTTTCTGAA GAAAGAGCTG 1080
  ATCATCCATT GTGTATTAAA CATATTGCTA CTAATGCTGT TTTGGGTAGA TGTGTTTCTC 1140
  CATAATAAAA AGAAGAAAGC TGAAAAACTC TGTCCCTTCC AACAAGACCC AGAGCACTGT 1200
  AGTATCAGGG GTAAAATGAA AGTATGTTC TCTGCTGCAT CCAGACTTCA TAAAAGCTGG 1260
  AGCTTAATCT AGAAAAAAAA TCAGAAAGAA ATTACACTGT GAGAACAGGT GCAATTCACT 1320
  TTTCCTTTAC ACAGAGTAAT ACTGGTAACT CATGGATGAA GGCTTAAGGG AATGAAATTG 1380
  GACTCACAGT ACTGAGTCAT CACACTGAAA ATGCAACCT GATACATCAG CAGAAGGTTT 1440
  ATGGGGGAAA AATGCAGCCT TCCAATTAAG CCAGATATCT GTATGACCAA GCTGCTCCAG 1500
  AATTAGTCAC TCAAAATCTC TCAGATTAAA TTATCAACTG TCACCAACCA TTCCTATGCT 1560
  GACAAGGCAA TTGCTTGTTC TCTGTGTTCC TGATACTACA AGGCTCTTCC TGACTTCCTA 1620
  AGATGCATT ATAAAATCT TATAATTCAC ATTTCTCCCT AAACTTTGAC TCAATCATGG 1680
  TATGTTGGCA AATATGGTAT ATTACTATTC AAATTGTTTT CCTTGTACCC ATATGTAATG 1740
  GGTCTTGTGA ATGTGCTCTT TTGTTCCTTT AATCATAATA AAAACATGTT TAAGCCTGCA 1800
  GGATCCCGGG AATTCAAGCT T                                          1821
```

```
CTGCAGGATC CCGGGAATTC AAGCTTATGG GTTCTATTGG TGCTGCTTCT ATGGAATATT 60
GTTATGATGT TTATAAAGAA TTGAAAGTTC ATCATGCTAA TGAAAATATT TATTATTGTC 120
CAATTGCTAT TATGTCTGCT TTGGCTATGG TTTATTTGGG TGCTAAAGAT TCTACTAGAA 180
CTCAAATTAA TAAAGTTGTT AGATATGATA AATTGCCAGG TTATGGTGAT TCTATTGAAG 240
CTCAATGTGG TACTTCTGTT AATGTTCATT CTTCTTTGAG AGATATTTTG AATCAAATTA 300
CTAAACCAAA TGATGTTTAT TCTTATTCTT TGGCTTCTAG ATTGTATGCT GAAGAAAGAT 360
ATCCAATTTT GCCAGAATAT TTGCAATGTG TTAAAGAATT GTATAGAGGT GGTTTGGAAC 420
CAATTAATTA TCAAACTGCT GCTGATCAAG CTAGAGAATT GATTAATTCT TGGGTTGAAT 480
CTCAAACTAA TGGTATTATT AGAAATGTTT TGCAACCATC TTCTGTTGAT CTCAAACTG 540
CTATGGTTTT GGTTAATGCT ATTGTTTATA AAGGTTTGTG GAAAAAACT TATAAAGATG 600
AAGATACTCA AGCTATGCCA TATAGAGTTA CTGAACAAGA ATCTAAACCA GTTCAAATGA 660
TGTATCAAAT TGGTTTGTAT AGAGTTGCTT CTATGGCTTC TGAAAAAATG AAAATTTGG 720
AATTGCCATA TGCTTCTGGT ACTATGTCTA TGTTGGTTTT GTTGCCAGAT GAAGTTTCTG 780
GTTTGGAACA ATTGGAATCT ATTATTAATT ATGAAAAATT GACTGAATGG ACTTCTTCTA 840
ATGTTATGGA AGAAAGAAAA ATTAAAGTTT ATTTGCCAAG AATGAAAATG GAAGAAAAAT 900
ATAATTTGAC TTCTGTTTTG ATGGCTATGG GTATTACTGA TGTTTATTCT TCTTCTGCTA 960
ATTTGTCTGG TATTTCTTCT GCTGAATCTT TGAAATTTC TCAAGCTGTT CATGCTGCTC 1020
ATGCTGAAAT TAATGAAGCT GGTAGAGAAG TTGTTGGTTC TGCTGAAGCT GGTGTTGATG 1080
CTGCTTCTGT TTCTGAAGAA TATAGAGCTG ATCATCCATA TTTGTATTGT ATTAAACATA 1140
TTGCTACTAA TGCTGTTTTG TATTATGGTA GATGTGTTTC TCCATAATAA AAGAAGAAA 1200
GCTGAAAAAC TCTGTCCCTT CCAACAAGAC CCAGAGCACT GTAGTATCAG GGGTAAAATG 1260
AAAAGTATGT TCTCTGCTGC ATCCAGACTT CATAAAAGCT GGAGCTTAAT CTAGAAAAAA 1320
AATCAGAAAG AAATTACACT GTGAGAACAG GTGCAATTCA CTTTTCCTTT ACACAGAGTA 1380
ATACTGGTAA CTCATGGATG AAGGCTTAAG GGAATGAAAT TGGACTCACA GTACTGAGTC 1440
ATCACACTGA AAAATGCAAC CTGATACATC AGCAGAAGGT TTATGGGGGA AAAATGCAGC 1500
CTTCCAATTA AGCCAGATAT CTGTATGACC AAGCTGCTCC AGAATTAGTC ACTCAAAATC 1560
TCTCAGATTA AATTATCAAC TGTCACCAAC CATTCCTATG CTGACAAGGC AATTGCTTGT 1620
TCTCTGTGTT CCTGATACTA CAAGGCTCTT CCTGACTTCC TAAAGATGCA TTATAAAAAT 1680
CTTATAATTC ACATTTCTCC CTAAACTTTG ACTCAATCAT GGTATGTTGG CAAATATGGT 1740
ATATTACTAT TCAAATTGTT TTCCTTGTAC CCATATGTAA TGGGTCTTGT GAATGTGCTC 1800
TTTTGTTCCT TTAATCATAA TAAAAACATG TTTAAGCCTG CAGGATCCCG GAATTCAAG 1860
CTT                                                          1863
```

```
CTGCAGGATC CCGGGAATTC AAGCTTATGC ATCATCATCA TCATCATGGT TCTATTGGTG    60
CTGCTTCTAT GGAATATTGT TATGATGTTT ATAAAGAATT GAAAGTTCAT CATGCTAATG   120
AAAATATTTA TTATTGTCCA ATTGCTATTA TGTCTGCTTT GGCTATGGTT TATTTGGGTG   180
CTAAAGATTC TACTAGAACT CAAATTAATA AAGTTGTTAG ATATGATAAA TTGCCAGGTT   240
ATGGTGATTC TATTGAAGCT CAATGTGGTA CTTCTGTTAA TGTTCATTCT TCTTTGAGAG   300
ATATTTTGAA TCAAATTACT AAACCAAATG ATGTTTATTC TTATTCTTTG GCTTCTAGAT   360
TGTATGCTGA AGAAAGATAT CCAATTTTGC CAGAATATTT GCAATGTGTT AAAGAATTGT   420
ATAGAGGTGG TTTGGAACCA ATTAATTATC AAACTGCTGC TGATCAAGCT AGAGAATTGA   480
TTAATTCTTG GGTTGAATCT CAAACTAATG GTATTATTAG AAATGTTTTG CAACCATCTT   540
CTGTTGATTC TCAAACTGCT ATGGTTTTGG TTAATGCTAT TGTTTATAAA GGTTTGTGGG   600
AAAAAACTTA TAAAGATGAA GATACTCAAG CTATGCCATA TAGAGTTACT GAACAAGAAT   660
CTAAACCAGT TCAAATGATG TATCAAATTG GTTTGTATAG AGTTGCTTCT ATGGCTTCTG   720
AAAAAATGAA AATTTTGGAA TTGCCATATG CTTCTGGTAC TATGTCTATG TTGGTTTTGT   780
TGCCAGATGA AGTTTCTGGT TTGGAACAAT GGAATCTAT TATTAATTAT GAAAAATTGA    840
CTGAATGGAC TTCTTCTAAT GTTATGGAAG AAAGAAAAAT TAAAGTTTAT TTGCCAAGAA   900
TGAAAATGGA AGAAAAATAT AATTTGACTT CTGTTTTGAT GGCTATGGGT ATTACTGATG   960
TTTATTCTTC TTCTGCTAAT TTGTCTGGTA TTTCTTCTGC TGAATCTTTG AAAATTTCTC  1020
AAGCTGTTCA TGCTGCTCAT GCTGAAATTA ATGAAGCTGG TAGAGAAGTT GTTGGTTCTG  1080
CTGAAGCTGG TGTTGATGCT GCTTCTGTTT CTGAAGAATA TAGAGCTGAT CATCCATATT  1140
TGTATTGTAT TAAACATATT GCTACTAATG CTGTTTTGTA TTATGGTAGA TGTGTTTCTC  1200
CATAATAAAA AGAAGAAAGC TGAAAACTC  TGTCCCTTCC AACAAGACCC AGAGCACTGT  1260
AGTATCAGGG GTAAAATGAA AAGTATGTTC TCTGCTGCAT CCAGACTTCA TAAAAGCTGG  1320
AGCTTAATCT AGAAAAAAAA TCAGAAAGAA ATTACACTGT GAGAACAGGT GCAATTCACT  1380
TTTCCTTTAC ACAGAGTAAT ACTGGTAACT CATGGATGAA GGCTTAAGGG AATGAAATTG  1440
GACTCACAGT ACTGAGTCAT CACACTGAAA AATGCAACCT GATACATCAG CAGAAGGTTT  1500
ATGGGGAAA AATGCAGCCT TCCAATTAAG CCAGATATCT GTATGACCAA GCTGCTCCAG   1560
AATTAGTCAC TCAAAATCTC TCAGATTAAA TTATCAACTG TCACCAACCA TTCCTATGCT  1620
GACAAGGCAA TTGCTTGTTC TCTGTGTTCC TGATACTACA AGGCTCTTCC TGACTTCCTA  1680
AAGATGCATT ATAAAAATCT TATAATTCAC ATTTCTCCCT AAACTTTGAC TCAATCATGG  1740
TATGTTGGCA AATATGGTAT ATTACTATTC AAATTGTTTT CCTTGTACCC ATATGTAATG  1800
GGTCTTGTGA ATGTGCTCTT TTGTTCCTTT AATCATAATA AAAACATGTT TAAGCCTGCA  1860
GGATCCCGGG AATTCAAGCT T                                            1881
```

```
TCTTCAACAACCAAGAGACGACTTCGACCACAACTACGACGAAGACAAAGAC   TTCTTTCTCGACTAGTAGTAACACATAATTTGTATAACGATGATTACGA ◆
AGAAGTTGTTGGTTCTCTGCTGAAGCTGGTGTTGATGCTGCTTCTGTTTCTG ◆ AAGAAAGAGCTGATCATCATTGTGTATTAAACATATTGCTACTAATGCT

CAAAACCCATCTACACAAAGAGGTATTATTTTCTTCTTTCGACTTTTTG   AGACAGGGAAGGTTGTTCTGGGTCTCGTGACATCATAGTCCCCATTTTAC ◆
GTTTTGGGTAGATGTGTTTCTCCATAATAAAAGAAGAAAGCTGAAAAAC ◆ TCTGTCCCTTCCAACAAGACCCAGAGCACTGTAGTATCAGGGGTAAAATG

TTTTCATACAAGAGACGACGTAGGTCTGAAGTATTTTCGACCTCGAATTA   GATCTTTTTTTAGTCTTTCTTTAATGTGACACTCTTGTCCACGTTAAGT ◆
AAAAGTATGTTCTCTGCTGCATCCAGACTTCATAAAAGCTGGAGCTTAAT ◆ CTAGAAAAAAAAATCAGAAGAGAAATTACACTGTGAGAACAGGTGCAATTCA

GAAAAGGAAAATGTGTCTCAGATTATGACCATTGAGTACCTACTTCCGAATTC   CCTTACTTTAACCTGAGTGTCATGACTCAGTAGTGTGACTTTTTACGTTG ◆
CTTTCCTTTACACAGAGTAATACTGGTAACTCATGGATGAAGGCTTAAG ◆ GGAATGAAATTGGACTCACAGTACTGAGTCATCACACTGAAAAATGCAAC

GACTATGTAGTCGTCTTCCAAATACCCCTTTTTACGTCGGAAGGTTAAT   TCGGTCTATAGACATACTGGTTCGACGAGGTCTTAATCAGTGAGTTTAG ◆
CTGATACATCAGCAGAAGGTTTATGGGGAAAAATGCAGCCTTCCAATTA ◆ AGCCAGATATCTGTATGACCAGCTGCTCCAGAATTAGTCACTCAAAATC

AGAGTCTAATTTAATAGTTGACAGTGGTTGGTAAGGATACGACTGTTCCG   TTAACGAACAAGAGACACAAGGACTATGATGTTCCGAGAAGGACTGAAGG ◆
TCTCAGATTAAATTATCAACTGTCACCAACCATTCCTATGCTGACAAGGC ◆ AATTGCTTGTTCTGTTCCTGATACTACAAGGCTCTTCCTGACTTCC

ATTTCTACGTAATATTTTTAGAATATTAAGTGTAAAGAGGGATTTGAAAC   TGAGTTAGTACCATACAACCGTTTATACCATATAATGATAAGTTTAACAA ◆
TAAAGATGCATTATAAAAATCTTATATTCACATTTCTCCCTAAACTTTG ◆ ACTCAATCATGTAGTTGGCAAATATGGTATATTACTATTCAAATTGTT

AAGGAACATGGGTATACATTACCCAGAACACTTACCACGAGAAAACAAGGA   AATTAGTATTATTTTTGTACAAATTCGGACGTTCCTAGGGCCCTTAAGTTC
TTCCTTGTACCCATATGTAATGGGTCTTGTGAATGTGCTCTTTTGTTCCT ◆ TTAATCATAATAAAAACATGTTTAAGCCTGCAGGATCCCGGGAATTCAAG

GAA ◆
CTT ◆
```

FIG. 11B

```
LOCUS        BOVCASA           1123 bp ss-mRNA MAM   15-SEP-1990
DEFINITION   Bovine alpha-s1-casein mRNA, complete cds.
ACCESSION    M33123
KEYWORDS     alpha-s1-casein.
SOURCE       Bovine (strain Holstein) lactating mammary gland, cDNA
to mRNA,  clone p-alpha-s1 C228.
  ORGANISM   Bos taurus
             Eukaryota; Animalia; Chordata; Vertebrata; Mammalia;
Theria; Eutheria; Artiodactyla; Ruminantia; Pecora; Bovoidea;
Bovinae; Bovini.
REFERENCE    1  (bases 1 to 1123)
  AUTHORS    Nagao,M., Maki,M., Sasaki,R. and Chiba,R.
  TITLE      Isolation and sequence analysis of bovine alpha-s1-
casein cDNA
             clone
  JOURNAL    Agric. Biol. Chem. 48, 1663-1667 (1984)
  STANDARD   full automatic
FEATURES             Location/Qualifiers
     mRNA            <1..1123
                     /note="alpha-s1-casein mRNA"
     sig_peptide     64..108
                     /codon_start=1
                     /note="alpha-s1-casein signal peptide"
     mat_peptide     109..705
                     /codon_start=1
                     /note="alpha-s1-casein"
     CDS             64..708
                     /note="alpha-s1-casein precursor"
                     /codon_start=1
```

/translation="MKLLILTCLVAVALARPKHPIKHQGLPQEVLNENLLRFFVAPFP

EVFGKEKVNELSKDIGSESTEDQAMEDIKQMEAESISSSEEIVPNSVEQKHIQKEDVP

SERYLGYLEQLLRLKKYKVPQLEIVPNSAEERLHSMKEGIHAQQKEPMIGVNQELAYF

YPELFRQFYQLDAYPSGAWYYVPLGTQYTDAPSFSDIPNPIGSENSEKTTMPLW"
```
BASE COUNT      331 a    247 c    223 g    322 t
ORIGIN
        1 tcacttcgac catcaaccca gcttgctgtt cttcccagtc ttgggttcaa
       51 gatcttgaca accatgaaac ttctcatcct tacctgtctt gtggctgttg
      101 ctcttgccag gcccaaacat cctatcaagc accaaggact ccctcaagaa
      151 gtcctcaatg aaaatttact caggtttttt gtggcacctt ttccagaagt
      201 gtttggaaag gagaaggtca atgaactgag caaggatatt gggagtgaat
      251 caactgagga tcaagccatg gaagatatta agcaaatgga agctgaaagc
      301 atttcgtcaa gtgaggaaat tgttcccaat agtgttgagc agaagcacat
      351 tcaaaaggaa gatgtgccct ctgagcgtta cctgggttat ctgaacagc
      401 ttctcagact gaaaaaatac aaagtacccc agctggaaat tgttcccaat
```

FIG. 12

```
 451 agtgctgagg aacgacttca cagtatgaaa gagggaatcc atgcccaaca
 501 gaaagaacct atgataggag tgaatcagga actggcctac ttctaccctg
 551 agcttttcag acaattctac cagctggatg cctatccatc tggtgcttgg
 601 tattacgttc cactaggcac acaatacact gatgcccat cattctctga
 651 catccctaat cccattggct ctgagaacag tgaaaagact actatgccac
 701 tgtggtgaag agtcaagtga attctgaggg actccacagt tatggtcttt
 751 gatgggtctg aaaattccat gctctacatg tcgcctcatc tacatgtcaa
 801 accattcatc caaaggcttc aactgctgtt ttagaacagg gcaatctcaa
 851 actgaggcac tccttgatgc tctactgtat tttagatagt gtaacatcct
 901 taagtgaaat tgtcctaaca gcttgttacc taaattccag tagtatcatg
 951 ctggtataaa ggccactgag tcaaagggaa ttaaagtctt cattaaattt
1001 ctgtatggaa aatgttttaa aagcctttga atcacttctc ctgtaagtgc
1051 catcatatca aataattgtg tgcattaact gagattttgt ctttcttctt
1101 ttcaataaat tacattttaa ggc
```

FIG. 12 (continued).

```
1    RPKHPIKHQG LPQEVLNENL LRFFVAPFPE VFGKEKVNEL SKDIGSESTE
51   DQAMEDIKQM EAESISSSEE IVPNSVEQKH IQKEDVPSER YLGYLEQLLR
101  LKKYKVPQLE IVPNSAEERL HSMKEGIHAQ QKEPMIGVNQ ELAYFYPELF
151  RQFYQLDAYP SGAWYYVPLG TQYTDAPSFS DIPNPIGSEN SEKTTMPLW
```

FIG. 13

```
1    MRPKHPIKHQ GLPQEVLNEN LLRVAPPEVG KEKVNELSKD IGSESTEDQA
51   MEDIKQMEAE SISSSEEIVP NSVEQKHIQK EDVPSERYLG YLEQLLRLKK
101  YKVPQLEIVP NSAEERLHSM KEGIHAQQKE PMIGVNQELA YYPELRQYQL
151  DAYPSGAWYY VPLGTQYTDA PSSDIPNPIG SENSEKTTMP LW
```

FIG. 14

```
ATGAGACCAA AACATCCAAT TAAACATCAA GGTTTGCCAC AAGAAGTTTT GAATGAAAAT    60

TTGTTGAGAG TTGCTCCACC AGAAGTTGGT AAAGAAAAAG TTAATGAATT GTCTAAAGAT   120

ATTGGTTCTG AATCTACTGA AGATCAAGCT ATGGAAGATA TTAAACAAAT GGAAGCTGAA   180

TCTATTTCTT CTTCTGAAGA AATTGTTCCA AATTCTGTTG AACAAAAACA TATTCAAAAA   240

GAAGATGTTC CATCTGAAAG ATATTTGGGT TATTTGGAAC AATTGTTGAG ATTGAAAAAA   300

TATAAAGTTC CACAATTGGA AATTGTTCCA AATTCTGCTG AAGAAAGATT GCATTCTATG   360

AAAGAAGGTA TTCATGCTCA ACAAAAAGAA CCAATGATTG GTGTTAATCA AGAATTGGCT   420

TATTATCCAG AATTGAGACA ATATCAATTG GATGCTTATC CATCTGGTGC TTGGTATTAT   480

GTTCCATTGG GTACTCAATA TACTGATGCT CCATCTTCTG ATATTCCAAA TCCAATTGGT   540

TCTGAAAATT CTGAAAAAAC TACTATGCCA TTGTGGTGAT GA                      582
```

FIG. 15

```
CTGCAGGATC CCGGGAATTC TAGAAGCTTA TGAGACCAAA ACATCCAATT AAACATCAAG    60
GTTTGCCACA AGAAGTTTTG AATGAAAATT TGTTGAGAGT TGCTCCACCA GAAGTTGGTA   120
AAGAAAAAGT TAATGAATTG TCTAAAGATA TTGGTTCTGA ATCTACTGAA GATCAAGCTA   180
TGGAAGATAT TAAACAAATG GAAGCTGAAT CTATTTCTTC TTCTGAAGAA ATTGTTCCAA   240
ATTCTGTTGA ACAAAAACAT ATTCAAAAAG AAGATGTTCC ATCTGAAAGA TATTTGGGTT   300
ATTTGGAACA ATTGTTGAGA TTGAAAAAAT ATAAAGTTCC ACAATTGGAA ATTGTTCCAA   360
ATTCTGCTGA AGAAAGATTG CATTCTATGA AGAAGGTAT TCATGCTCAA CAAAAAGAAC   420
CAATGATTGG TGTTAATCAA GAATTGGCTT ATTATCCAGA ATTGAGACAA TATCAATTGG   480
ATGCTTATCC ATCTGGTGCT TGGTATTATG TTCCATTGGG TACTCAATAT ACTGATGCTC   540
CATCTTCTGA TATTCCAAAT CCAATTGGTT CTGAAAATTC TGAAAAAACT ACTATGCCAT   600
TGTGGTGATG AAAGAGTCAA GTGAATTCTG AGGGACTCCA CAGTTATGGT CTTTGATGGG   660
TCTGAAAATT CCATGCTCTA CATGTCGCCT CATCTACATG TCAAACCATT CATCCAAAGG   720
CTTCAACTGC TGTTTTAGAA CAGGGCAATC TCAAACTGAG GCACTCCTTG ATGCTCTACT   780
GTATTTTAGA TAGTGTAACA TCCTTAAGTG AAATTGTCCT AACAGCTTGT TACCTAAATT   840
CCAGTAGTAT CATGCTGGTA TAAAGGCCAC TGAGTCAAAG GGAATTAAAG TCTTCATTAA   900
ATTTCTGTAT GGAAAATGTT TTAAAAGCCT TGAATCACT TCTCCTGTAA GTGCCATCAT    960
ATCAAATAAT TGTGTGCATT AACTGAGATT TTGTCTTTCT TCTTTTCAAT AAATTACATT  1020
TTAAGGCCTG CAGGATCCCG GGAATTCTAG AAGCTT                            1056
```

FIG. 16

5' AATCAGGATCCCGGGCATAT 3'
　　　　　　　　　　　　 ┌─── CASEIN 1 ───
5' AATCAGGATCCCGGGCATATGAGACCAAAACATTAAACATCCAATTAAACATCAAGGTTGCCACAAGAAGTTTGAACGAAAA--

-CTTGTTGAGATACTACGTTGCTCCAT 3'
3' CTCTATGATGCAACGAGGTAGGTCTTCAAATGCCATTCTTTTTCAATTACTTAACAGATTTCTATAGCCA-
　　　　　　　　　　　　　　　　 ─── CASEIN 2 ───

┌─── CASEIN 3 ───
　　　　　　　　　　5' ATCAAGCCATGGAAGATATTAAACAAATGGAAGCTGAATCTATCTCTTCTTCTGAAGAAATCG-
-AGACTTAGATGACTTCTAGTTCGGTACCTTCTATAA 5'

-TCCCAAACTCTGTTGAACAAAAACATATTCAAAAAGAAGACGTCCCATC 3'
　　　　　　　　　　　　　　　　　　　　　　　 3' GTTTTTCTTCTGCAGGGTAGACTTTCTATGAACCCAATGAATCTTGTTAA
CAACTCTAACTTTTTTATGTTTCAAGGTGTTAACCTTTAGCAGGGTTTGAGTCGACTTCT 5'
　　　　　　　　　　　　　　　　　　　　　　3' CAGGGTTTGAGTCGACTTCT 5'
─── CASEIN 4 ───

FIG. 17A

CASEIN 5

5' CAAAAAGAAGACGTCCCATC 3'
5' CAAAAAGAAGACGTCCCATCTGAAAGATACTTGGGT-
TACTTAGAACAATTGTTGAGATTGAAAAAATACAAAGTTCCACAATTGGAAATCGTCCCAAACTCAGCTGAAGA 3'
3' CAAGGTTTGAGTCGACTTCTTTCTAACGTAAGATACTTTCTTCCAT-

CASEIN 7

5' TTGGCTTACTACTACCCAGAATTGTACAGACAATACTATCAATTGGATGCTTACCC
AAGTACGAGTTGTTTTCTTGGTTACTAACCACAATTGGTTCTTAACCGAATGATGATGGGTCT 5'

CASEIN 6

-ATCTGGTGCTTGGTACTACGTTCCTTTAGGTACCCAATACACTG 3'
3' AAATCCATGGGTTATGTGACTACGAGGTAGAATGAGACTATAAGGTTTGGGTTAGCCAAGACTTTTGAGACTTTTT-

CASEIN 8

3' GTTAGCCAAGACTTTTGAGACTTTTT-

TGATGATACGGTAACACCATTATTCGAATCCGGATTCAG 5'
TGATGATACGGTAACACCATTATTCGAAGTACTAG 5'

FIG. 17B

```
AATCAGGATCCCGGGCATATGAGACCAAAACATCCAATTAAACATCAAGGTTTGCCACAA
----.----+----.----+----.----+----.----+----.----+----.----+  60
TTAGTCCTAGGGCCCGTATACTCTGGTTTTGTAGGTTAATTTGTAGTTCCAAACGGTGTT

N   Q   D   P   G   H   M   R   P   K   H   P   I   K   H   Q   G   L   P   Q

GAAGTTTTGAACGAAAACTTGTTGAGATACTACGTTGCTCCATACCCAGAAGTTTACGGT
----.----+----.----+----.----+----.----+----.----+----.----+  120
CTTCAAAACTTGCTTTTGAACAACTCTATGATGCAACGAGGTATGGGTCTTCAAATGCCA

E   V   L   N   E   N   L   L   R   Y   Y   V   A   P   Y   P   E   V   Y   G

AAAGAAAAAGTTAATGAATTGTCTAAAGATATCGGTTCTGAATCTACTGAAGATCAAGCC
----.----+----.----+----.----+----.----+----.----+----.----+  180
TTTCTTTTTCAATTACTTAACAGATTTCTATAGCCAAGACTTAGATGACTTCTAGTTCGG

K   E   K   V   N   E   L   S   K   D   I   G   S   E   S   T   E   D   Q   A

ATGGAAGATATTAAACAAATGGAAGCTGAATCTATCTCTTCTTCTGAAGAAATCGTCCCA
----.----+----.----+----.----+----.----+----.----+----.----+  240
TACCTTCTATAATTTGTTTACCTTCGACTTAGATAGAGAAGAAGACTTCTTTAGCAGGGT

M   E   D   I   K   Q   M   E   A   E   S   I   S   S   S   E   E   I   V   P
                                          *
AACTCTGTTGAACAAAAACATATTCAAAAAGAAGACGTCCCATCTGAAAGATACTTGGGT
----.----+----.----+----.----+----.----+----.----+----.----+  300
TTGAGACAACTTGTTTTTGTATAAGTTTTTCTTCTGCAGGGTAGACTTTCTATGAACCCA

N   S   V   E   Q   K   H   I   Q   K   E   D   V   P   S   E   R   Y   L   G

TACTTAGAACAATTGTTGAGATTGAAAAAATACAAAGTTCCACAATTGGAAATCGTCCCA
----.----+----.----+----.----+----.----+----.----+----.----+  360
ATGAATCTTGTTAACAACTCTAACTTTTTTATGTTTCAAGGTGTTAACCTTTAGCAGGGT

Y   L   E   Q   L   L   R   L   K   K   Y   K   V   P   Q   L   E   I   V   P

AACTCAGCTGAAGA
----.----+----  374
TTGAGTCGACTTCT
  N   S   A   E   E
```

FIG. 18A

```
AATCAGGATCCCGGGCATATGAGACCAAAACATCCAATTAAACATCAAGGTTTGCCACAA
----.----+----.----+----.----+----.----+----.----+----.----+   60
TTAGTCCTAGGGCCCGTATACTCTGGTTTTGTAGGTTAATTTGTAGTTCCAAACGGTGTT

N   Q   D   P   G   H   M   R   P   K   H   P   I   K   H   Q   G   L   P   Q

GAAGTTTTGAACGAAAACTTGTTGAGATACTACGTTGCTCCATACCCAGAAGTTTACGGT
----.----+----.----+----.----+----.----+----.----+----.----+  120
CTTCAAAACTTGCTTTTGAACAACTCTATGATGCAACGAGGTATGGGTCTTCAAATGCCA

E   V   L   N   E   N   L   L   R   Y   Y   V   A   P   Y   P   E   V   Y   G

AAAGAAAAAGTTAATGAATTGTCTAAAGATATCGGTTCTGAATCTACTGAAGATCAAGCC
----.----+----.----+----.----+----.----+----.----+----.----+  180
TTTCTTTTTCAATTACTTAACAGATTTCTATAGCCAAGACTTAGATGACTTCTAGTTCGG

K   E   K   V   N   E   L   S   K   D   I   G   S   E   S   T   E   D   Q   A

ATGGAAGATATTAAACAAATGGAAGCTGAATCTATCTCTTCTTCTGAAGAAATCGTCCCA
----.----+----.----+----.----+----.----+----.----+----.----+  240
TACCTTCTATAATTTGTTTACCTTCGACTTAGATAGAGAAGAAGACTTCTTTAGCAGGGT

M   E   D   I   K   Q   M   E   A   E   S   I   S   S   S   E   E   I   V   P

AACTCTGAACAAAAACATATTCAAAAGAAGACGTCCCATCTGAAAGATACTTGGGTTAC
----.----+----.----+----.----+----.----+----.----+----.----+  300
TTGAGACTTGTTTTTGTATAAGTTTTTCTTCTGCAGGGTAGACTTTCTATGAACCCAATG

N   S   E   Q   K   H   I   Q   K   E   D   V   P   S   E   R   Y   L   G   Y

TTAGAACAATTGTTGAGATTGAAAAAATACAAAGTTCCACAATTGGAAATCGTCCCAAC
----.----+----.----+----.----+----.----+----.----+----.----+  360
AATCTTGTTAACAACTCTAACTTTTTTATGTTTCAAGGTGTTAACCTTTAGCAGGGTTG

L   E   Q   L   L   R   L   K   K   Y   K   V   P   Q   L   E   I   V   P   N

TCAGCTGAAGA
----.----+-  371
AGTCGACTTCT

```
CAAAAAGAAGACGTCCCATCTGAAAGATACTTGGGTTACTTAGAACAATTGTTGAGATTG
----.----+----.----+----.----+----.----+----.----+----.----+   60
GTTTTTCTTCTGCAGGGTAGACTTTCTATGAACCCAATGAATCTTGTTAACAACTCTAAC

Q   K   E   D   V   P   S   E   R   Y   L   G   Y   L   E   Q   L   L   R   L

AAAAAATACAAAGTTCCACAATTGGAAATCGTCCCAAACTCAGCTGAAGAAAGATTGCAT
----.----+----.----+----.----+----.----+----.----+----.----+   120
TTTTTTATGTTTCAAGGTGTTAACCTTTAGCAGGGTTTGAGTCGACTTCTTTCTAACGTA

K   K   Y   K   V   P   Q   L   E   I   V   P   N   S   A   E   E   R   L   H

TCTATGAAAGAAGGTATTCATGCTCAACAAAAAGAACCAATGATTGGTGTTAACCAAGAA
----.----+----.----+----.----+----.----+----.----+----.----+   180
AGATACTTTCTTCCATAAGTACGAGTTGTTTTTCTTGGTTACTAACCACAATTGGTTCTT

S   M   K   E   G   I   H   A   Q   Q   K   E   P   M   I   G   V   N   Q   E

TTGGCTTACTACTACCCAGAATTGTACAGACAATACTATCAATTGGATGCTTACCCATCT
----.----+----.----+----.----+----.----+----.----+----.----+   240
AACCGAATGATGATGGGTCTTAACATGTCTGTTATGATAGTTAACCTACGAATGGGTAGA

L   A   Y   Y   Y   P   E   L   Y   R   Q   Y   Y   Q   L   D   A   Y   P   S

*
GGTGCTTGGTACTACGTTCCTTTAGGTACCCAATACACTGATGCTCCATCTTACTCTGAT
----.----+----.----+----.----+----.----+----.----+----.----+   300
CCACGAACCATGATGCAAGGAAATCCATGGGTTATGTGACTACGAGGTAGAATGAGACTA

G   A   W   Y   Y   V   P   L   G   T   Q   Y   T   D   A   P   S   Y   S   D

ATTCCAAACCCAATCGGTTCTGAAAACTCTGAAAAAACTACTATGCCATTGTGGTAATAA
----.----+----.----+----.----+----.----+----.----+----.----+   360
TAAGGTTTGGGTTAGCCAAGACTTTTGAGACTTTTTTGATGATACGGTAACACCATTATT

I   P   N   P   I   G   S   E   N   S   E   K   T   T   M   P   L   W

GCTTCATGATC
----.----+-   371
CGAAGTACTAG
```

FIG. 19A

```
CAAAAAGAAGACGTCCCATCTGAAAGATACTTGGGTTACTTAGAACAATTGTTGAGATTG
----.----+----.----+----.----+----.----+----.----+----.----+   60
GTTTTTCTTCTGCAGGGTAGACTTTCTATGAACCCAATGAATCTTGTTAACAACTCTAAC

Q  K  E  D  V  P  S  E  R  Y  L  G  Y  L  E  Q  L  L  R  L

AAAAAATACAAAGTTCCACAATTGGAAATCGTCCCAAACTCAGCTGAAGAAAGATTGCAT
----.----+----.----+----.----+----.----+----.----+----.----+   120
TTTTTTATGTTTCAAGGTGTTAACCTTTAGCAGGGTTTGAGTCGACTTCTTTCTAACGTA

K  K  Y  K  V  P  Q  L  E  I  V  P  N  S  A  E  E  R  L  H

TCTATGAAAGAAGGTATTCATGCTCAACAAAAAGAACCAATGATTGGTGTTAACCAAGAA
----.----+----.----+----.----+----.----+----.----+----.----+   180
AGATACTTTCTTCCATAAGTACGAGTTGTTTTTCTTGGTTACTAACCACAATTGGTTCTT

S  M  K  E  G  I  H  A  Q  Q  K  E  P  M  I  G  V  N  Q  E

TTGGCTTACTACTACCCAGAATTGTACAGACAATACTATCAATTGGATGCTTACCCATCT
----.----+----.----+----.----+----.----+----.----+----.----+   240
AACCGAATGATGATGGGTCTTAACATGTCTGTTATGATAGTTAACCTACGAATGGGTAGA

L  A  Y  Y  Y  P  E  L  Y  R  Q  Y  Y  Q  L  D  A  Y  P  S

*
GGTGCTTTGTACTACGTTCCTTTAGGTACCCAATACACTGATGCTCCATCTTACTCTGAT
----.----+----.----+----.----+----.----+----.----+----.----+   300
CCACGAAACATGATGCAAGGAAATCCATGGGTTATGTGACTACGAGGTAGAATGAGACTA

G  A  L  Y  Y  V  P  L  G  T  Q  Y  T  D  A  P  S  Y  S  D

ATTCCAAACCCAATCGGTTCTGAAAACTCTGAAAAAACTACTATGCCATTGTGGTAATAA
----.----+----.----+----.----+----.----+----.----+----.----+   360
TAAGGTTTGGGTTAGCCAAGACTTTTGAGACTTTTTTGATGATACGGTAACACCATTATT

I  P  N  P  I  G  S  E  N  S  E  K  T  T  M  P  L  W

GCTTCATGATC
----.----+-   371
CGAAGTACTAG
```

FIG. 19B

```
     5'GATCCCGGGCtgcaGAGACCAAAAC-3'
AATCAGGATCCCGGGCATATGAGACCAAAACATCCAATTAAACATCAAGGTTTGCCACAA
----.----+----.----+----.----+----.----+----.----+----.----+   60
TTAGTCCTAGGGCCCGTATACTCTGGTTTTGTAGGTTAATTTGTAGTTCCAAACGGTGTT
     N  Q  D  P  G  H  M  R  P  K  H  P  I  K  H  Q  G  L  P  Q GAAGTTTTGAACGAAAACTTGTTGAGATACTACGTTGCTCCATACCCAGAAGTTTACGGT
----.----+----.----+----.----+----.----+----.----+----.----+  120
CTTCAAAACTTGCTTTTGAACAACTCTATGATGCAACGAGGTATGGGTCTTCAAATGCCA
  E  V  L  N  E  N  L  L  R  Y  Y  V  A  P  Y  P  E  V  Y  G AAAGAAAAAGTTAATGAATTGTCTAAAGATATCGGTTCTGAATCTACTGAAGATCAAGCC
----.----+----.----+----.----+----.----+----.----+----.----+  180
TTTCTTTTTCAATTACTTAACAGATTTCTATAGCCAAGACTTAGATGACTTCTAGTTCGG
  K  E  K  V  N  E  L  S  K  D  I  G  S  E  S  T  E  D  Q  A ATGGAAGATATTAAACAAATGGAAGCTGAATCTATCTCTTCTTCTGAAGAAATCGTCCCA
----.----+----.----+----.----+----.----+----.----+----.----+  240
TACCTTCTATAATTTGTTTACCTTCGACTTAGATAGAGAAGAAGACTTCTTTAGCAGGGT
  M  E  D  I  K  Q  M  E  A  E  S  I  S  S  S  E  E  I  V  P AACTCTGAACAAAAACATATTCAAAAGAAGACGTCCCATCTGAAAGATACTTGGGTTAC
----.----+----.----+----.----+----.----+----.----+----.----+  300
TTGAGACTTGTTTTTGTATAAGTTTTTCTTCTGCAGGGTAGACTTTCTATGAACCCAATG
  N  S  E  Q  K  H  I  Q  K  E  D  V  P  S  E  R  Y  L  G  Y TTAGAACAATTGTTGAGATTGAAAAAATACAAAGTTCCACAATTGGAAATCGTCCCAAAC
----.----+----.----+----.----+----.----+----.----+----.----+  360
AATCTTGTTAACAACTCTAACTTTTTTATGTTTCAAGGTGTTAACCTTTAGCAGGGTTTG
  L  E  Q  L  L  R  L  K  K  Y  K  V  P  Q  L  E  I  V  P  N TCAGCTGAAGAAAGATTGCATTCTATGAAAGAAGGTATTCATGCTCAACAAAAAGAACCA
----.----+----.----+----.----+----.----+----.----+----.----+  420
AGTCGACTTCTTTCTAACGTAAGATACTTTCTTCCATAAGTACGAGTTGTTTTTCTTGGT
  S  A  E  E  R  L  H  S  M  K  E  G  I  H  A  Q  Q  K  E  P ATGATTGGTGTTAACCAAGAATTGGCTTACTACTACCCAGAATTGTACAGACAATACTAT
----.----+----.----+----.----+----.----+----.----+----.----+  480
TACTAACCACAATTGGTTCTTAACCGAATGATGATGGGTCTTAACATGTCTGTTATGATA
  M  I  G  V  N  Q  E  L  A  Y  Y  Y  P  E  L  Y  R  Q  Y  Y CAATTGGATGCTTACCCATCTGGTGCTTTGTACTACGTTCCTTTAGGTACCCAATACACT
----.----+----.----+----.----+----.----+----.----+----.----+  540
GTTAACCTACGAATGGGTAGACCACGAAACATGATGCAAGGAAATCCATGGGTTATGTGA
  Q  L  D  A  Y  P  S  G  A  L  Y  Y  V  P  L  G  T  Q  Y  T GATGCTCCATCTTACTCTGATATTCCAAACCCAATCGGTTCTGAAAACTCTGAAAAAACT
----.----+----.----+----.----+----.----+----.----+----.----+  600
CTACGAGGTAGAATGAGACTATAAGGTTTGGGTTAGCCAAGACTTTTGAGACTTTTTTGA
  D  A  P  S  Y  S  D  I  P  N  P  I  G  S  E  N  S  E  K  T ACTATGCCATTGTGGTAATAAGCTTCATGATC
----.----+----.----+----.----+--  632
TGATACGGTAACACCATTATTCGAAGTACTAG
   3'GGTAACACCATTATTCGAAGTACTAG-5'*
```

FIG. 20

```
                    PstI
AATCAGGATCCCGGGCTGCAGAGACCAAAACATCCAATTAAACATCAAGGTTTGCCACAA
----.----+----.----+----.----+----.----+----.----+----.----+   60
TTAGTCCTAGGGCCCGACGTCTCTGGTTTTGTAGGTTAATTTGTAGTTCCAAACGGTGTT
    N  Q  D  P  G  H  M  R  P  K  H  P  I  K  H  Q  G  L  P  Q

GAAGTTTTGAACGAAAACTTGTTGAGATACTACGTTGCTCCATACCCAGAAGTTTACGGT
----.----+----.----+----.----+----.----+----.----+----.----+  120
CTTCAAAACTTGCTTTTGAACAACTCTATGATGCAACGAGGTATGGGTCTTCAAATGCCA
    E  V  L  N  E  N  L  L  R  Y  Y  V  A  P  Y  P  E  V  Y  G

AAAGAAAAAGTTAATGAATTGTCTAAAGATATCGGTTCTGAATCTACTGAAGATCAAGCC
----.----+----.----+----.----+----.----+----.----+----.----+  180
TTTCTTTTTCAATTACTTAACAGATTTCTATAGCCAAGACTTAGATGACTTCTAGTTCGG
    K  E  K  V  N  E  L  S  K  D  I  G  S  E  S  T  E  D  Q  A

ATGGAAGATATTAAACAAATGGAAGCTGAATCTATCTCTTCTTCTGAAGAAATCGTCCCA
----.----+----.----+----.----+----.----+----.----+----.----+  240
TACCTTCTATAATTTGTTTACCTTCGACTTAGATAGAGAAGAAGACTTCTTTAGCAGGGT
    M  E  D  I  K  Q  M  E  A  E  S  I  S  S  S  E  E  I  V  P

AACTCTGAACAAAAACATATTCAAAAGAAGACGTCCCATCTGAAAGATACTTGGGTTAC
----.----+----.----+----.----+----.----+----.----+----.----+  300
TTGAGACTTGTTTTTGTATAAGTTTTTCTTCTGCAGGGTAGACTTTCTATGAACCCAATG
    N  S  E  Q  K  H  I  Q  K  E  D  V  P  S  E  R  Y  L  G  Y

TTAGAACAATTGTTGAGATTGAAAAAATACAAAGTTCCACAATTGGAAATCGTCCCAAAC
----.----+----.----+----.----+----.----+----.----+----.----+  360
AATCTTGTTAACAACTCTAACTTTTTTATGTTTCAAGGTGTTAACCTTTAGCAGGGTTTG
    L  E  Q  L  L  R  L  K  K  Y  K  V  P  Q  L  E  I  V  P  N

TCAGCTGAAGAAAGATTGCATTCTATGAAAGAAGGTATTCATGCTCAACAAAAAGAACCA
----.----+----.----+----.----+----.----+----.----+----.----+  420
AGTCGACTTCTTTCTAACGTAAGATACTTTCTTCCATAAGTACGAGTTGTTTTTCTTGGT
    S  A  E  E  R  L  H  S  M  K  E  G  I  H  A  Q  Q  K  E  P

ATGATTGGTGTTAACCAAGAATTGGCTTACTACTACCCAGAATTGTACAGACAATACTAT
----.----+----.----+----.----+----.----+----.----+----.----+  480
TACTAACCACAATTGGTTCTTAACCGAATGATGATGGGTCTTAACATGTCTGTTATGATA
    M  I  G  V  N  Q  E  L  A  Y  Y  Y  P  E  L  Y  R  Q  Y  Y

CAATTGGATGCTTACCCATCTGGTGCTTTGTACTACGTTCCTTTAGGTACCCAATACACT
----.----+----.----+----.----+----.----+----.----+----.----+  540
GTTAACCTACGAATGGGTAGACCACGAAACATGATGCAAGGAAATCCATGGGTTATGTGA
    Q  L  D  A  Y  P  S  G  A  L  Y  Y  V  P  L  G  T  Q  Y  T

GATGCTCCATCTTACTCTGATATTCCAAACCCAATCGGTTCTGAAAACTCTGAAAAAACT
----.----+----.----+----.----+----.----+----.----+----.----+  600
CTACGAGGTAGAATGAGACTATAAGGTTTGGGTTAGCCAAGACTTTTGAGACTTTTTTGA
    D  A  P  S  Y  S  D  I  P  N  P  I  G  S  E  N  S  E  K  T

HindIII
ACTATGCCATTGTGGTAATAAGCTTCATGATC
----.----+----.----+----.----+--  632
TGATACGGTAACACCATTATTCGAAGTACTAG
                       └────┘
                          *
```

FIG. 21

PHENYLALANINE-FREE PROTEIN AND DNA CODING THEREFOR

This application is a 371 of PCT/GB94/01046 filed on May 16, 1994, which claims benefit of GB9310472 filed on May 20, 1993.

This invention relates to an edible protein which has been modified so that it is phenylalanine free, to DNA coding for it, and to a method of producing it. Such a protein is a useful nutrient in the treatment of diseases which are associated with difficulty in metabolising phenylalanine. A particular example of such a disease is phenylketonuria (PKU).

PKU is a genetically acquired disease that occurs in a relatively fixed proportion of new births in a human population. A defect in the enzyme carrying out the pterin-dependent hydroxylation of phenylalanine to tyrosine prevents the body from metabolizing the amino acid phenylalanine. This amino acid occurs in varying proportions in all proteins in foodstuffs and is, in the correct amount, essential for human protein synthesis, and therefore for the growth and maintenance of the body. Patients with PKU cannot remove excess phenylalanine from the blood and tissues and the failure to achieve this control over phenylalanine levels leads to grave neurological damage, especially in the growing child.

PKU patients are at present fed with a synthetic diet which contains a metabolically-correct amount of phenylalanine along with a mixture of the other amino acids needed for growth. Such a diet is unpalatable and is presented in liquid form only and therefore has difficulty in achieving patient compliance.

An object of this invention is to provide an edible protein which when pure contains no phenylalanine and which can form the basis for a diet containing the optimal nutritional phenylalanine content for PKU patients. This object may be achieved by taking the gene from a known nutritional protein and modifying it so that the codons coding for phenylalanine are deleted or are replaced by codons coding for another amino acid.

An alternative approach is to synthesise by chemical means DNA coding for a phenylalanine-free polypeptide, starting either from fragments of genes coding for existing proteins, or from the nucleotides themselves.

According to one aspect of the invention we provide a DNA molecule coding for a food protein, modified in that the codons coding for phenylalanine have been deleted or replaced by codons coding for one or more other amino acids.

According to another aspect of the invention we provide an edible polypeptide which comprises a food protein modified in that the phenylalanine residues have been omitted or have been replaced by one or more other amino acids also occurring in protein.

We further provide a nutrient material comprising an edible polypeptide as defined above and other edible substances.

The food protein is preferably a common food protein such as ovalbumin or caesin.

We also provide a nutrient material comprising an edible protein or modified food protein as hereinbefore defined, and other edible substances.

The protein according to the invention is phenylalanine free when pure, but the diet of the patient must contain some phenylalanine, i.e. the amount required for metabolism, but with substantially no excess.

An obvious approach would be to add an appropriate proportion of normal food proteins, which contain phenylalanine, to a pure phenylalanine-free protein according to the invention.

On the other hand, proteins are notoriously difficult to purify to a high level. If only partially purified, the phenylalanine-free protein will be accompanied by other protein products of the host organism containing their normal amounts of phenylalanine. Thus, if the modified protein is only partly purified (which is much easier than complete purification), a protein mixture containing overall a reduced proportion of phenylalanine will be obtained. By controlling the degree of purification, a protein mixture containing a metabolically-appropriate proportion of phenylalanine can be produced. This invention also provides such a mixture.

Although codons for phenylalanine may simply be deleted from the gene for a food protein, in order to preserve as far as possible the tertiary structure of the protein the codons coding for phenylalanine are preferably replaced by codons coding for another amino acid, preferably those having the most similar properties, e.g. tyrosine.

We also provide an expression vector into which has been incorporated DNA for an edible protein or modified food protein as described herein. The expression vector is preferably a *Saccharomyces cerevisiae* expression vector because this yeast has a long history as a human foodstuff and is amenable to genetic manipulation. Other yeasts, e.g. *Pischia pastoris*, may also be used.

We further provide a host, for example a yeast such as *S. cerevisiae* or *Pichia pastoris*, transformed by such an expression vector.

Ovalbumin and caesin have been selected as preferred food proteins to be modified in accordance with this invention because they are naturally-occurring proteins which are commonly used as human foodstuffs, are widely acceptable, and also because the modified proteins are likely to behave in a similar manner to the native proteins when cooked or subjected to other food processing steps. A wide variety of other food proteins may, however, also be chosen.

Preferably, apart from omitting or substituting codons coding for phenylalanine, the DNA molecule coding for the edible protein is modified as necessary to ensure that the codon for each amino acid is the codon of preference for the selected host, e.g. *S.cerevisiae*.

DNA sequences and polypeptides embodying the invention will now be described in more detail in non-limiting manner, with reference to the Figures and Examples. FIGS. 1 to 11 relate to modified chick ovalbumin and FIGS. 12 to 24 relate to modified bovine casein.

FIG. 1 shows the sequence of cDNA (SEQ ID NO:38) for unmodified chick ovalbumin (a copy of the Genbank entry).

FIG. 2 (SEQ ID NO:39) shows the primary sequence (386 amino acids) of the coding region (coordinates 66–1223) of the cDNA for chick ovalbumin (GenBank accession number V00383). The locations of the twenty phenylalanine residues are shown in bold face.

FIG. 3 (SEQ ID NO:1) shows a polyypeptide corresponding to that of FIG. 2, but from which all phenylalanine residues have been deleted.

FIG. 4 (SEQ ID NO:2) shows the amino acid sequence of a polypeptide corresponding to FIG. 2, in which the phenylalanine residues have been replaced by tyrosine residues.

FIG. 5 (SEQ ID NO:3) shows the DNA sequence (1098 bp) of a synthetic gene encoding the derivative of chick ovalbumin lacking phenylalanine (oval-f) produced using the optimal pattern of codon usage for *S. cerevisiae*.

FIG. 6 (SEQ ID NO:4) shows the DNA sequence (1158 bp) of a synthetic gene encoding the derivative of chick ovalbumin in which the phenylalanines are replaced by tyrosines (Y oval-f) produced using the optimal pattern of codon usage for *S. cerevisiae*.

FIGS. 7 to 10 (SEQ ID NO:5–8) show, respectively, the nucleotide sequence for the constructs pl+oval-f+3end, pl+h6oval-f+3end, pl+Yoval-f+3end, and pl+h6Yoval-f+3end.

FIGS. 11A and 11B (SEQ ID NO:5) show the nucleotide sequence of the double stranded synthetic pl+oval-f+3end gene constructed from overlapping oligonucleotides. The end points of the oligonucleotides are shown by the ♦ character.

FIG. 12 shows a copy of the GenBank entry for bovine alpha-S1-casein mRNA (SEQ ID NO:40) obtained using the FETCH program of the UWGCG suite of software.

FIG. 13 shows the primary amino acid sequence (SEQ ID NO:42) of the mature alpha-S1-casein specified by the coding region (coordinates 109–705) of the alpha-s1-casein mRNA (EMBL accession number M33123). The locations of the eight phenylalanine residues are shown in bold face.

FIG. 14 (SEQ ID NO:9) shows a modified protein corresponding to that of FIG. 13, but from which all phenylalanine residues have been deleted and an N-terminal methionine residue has been added.

FIG. 15 (SEQ ID NO:10) shows a DNA sequence (582 nucleotides) coding for the modified protein of FIG. 14, the derivative of mature bovine alpha-s1-casein lacking phenylalanine residues and possessing an N-terminal methionine residue produced using the optimal pattern of codon usage for S. cerevisiae. Two stop codons have also been added at the end of the casein coding sequence.

FIG. 16 (SEQ ID NO:11) shows the DNA sequence (1056 necleotides) of a synthetic gene encoding the derivative of mature bovine alpha-s1-casein lacking phenylalanine residues and pocessing an N-terminal methionine residue, produced using the optimal pattern of codon usage for S. cerevisaise. Two stop codons have also been added at the end of the casein coding sequence. The non-translated 3' region of bovine alpha-s1-casein mRNA had been added and the construct is bounded by polylinkers.

FIG. 17 (SEQ ID NO:26–37) shows the nucleotide sequences of bovine casein gene blocks A and B, from which the whole gene was subsequently assembled (Block A: PCR primers=SEQ ID NOS:26 and 31; casein 1=SEQ ID NO:27; casein 2=SEQ ID NO:28; casein 3=SEQ ID NO:29; casein 4=SEQ ID NO:30. Block B: PCR primers=SEQ ID NOS:32 and 37; casein 5=SEQ ID NO:33; casein 6=SEQ ID NO:34; casein 7=SEQ ID NO:35; casein 8=SEQ ID NO:36.).

FIG. 18*a* (SEQ ID NO:12–13) and 18*b* (SEQ ID NO:14–15) show respectively the predicted and actual DNA and protein sequences of block A. The TTG triplet deletion in the "actual" sequence obtained is indicated (*).

FIGS. 19*a* (SEQ ID NO:16–17) and 19*b* (SEQ ID NO:18–19) show respectively the predicted and actual DNA and protein sequences of block B. The single base change in the sequence is indicated (*).

FIG. 20 (SEQ ID NO:20–25) shows the combined DNA and protein sequences of blocks A and B. The mutagenic N-terminal (to create a unique *PstI* restriction site) and C-terminal oligonucleotide primers for PCR amplification are indicated (*).

FIG. 21 (SEQ ID NO:22–23) shows the complete DNA and protein sequences of the synthetic casein.

EXAMPLE 1

The gene and downstream non-translated DNA sequence for chick ovalbumin were based on the nucleotide sequence of the complementary cDNA for chick ovalbumin deposited by O'Hare et al in the GenBank database with the accession number V00383. The vector pEMBLyex4 (see Cesareni, G and Murray, J. A. H. (1987) In 'Genetic Engineering' (Ed. Setlow, J. K.) Volume 9 Plenum Publishing Corporation, New York, pp135–154) was chosen for expression, as it can be used to direct the expression of genes which lack their own promoter. The vector harbours a hybrid promoter consisting of the upstream activator sequence of the GAL1 promoter and the 5' non-translated leader of the CYC1 gene, up to position –4. The plasmid contains a translation initiation codon ATG downstream from the GAL1–CYC1 promoter. The codon ATG is followed by a unique HindIII site and is preceded by unique cloning sites for BamHI, PstI, SmaI and XbaI. In addition to yeast selectable markers and origin of replication it carries ampicillin resistance and a functional *E. coli* origin. The complete nucleotide sequence of the vector is known.

The sequence of the cDNA for chick ovalbumin is shown in FIG. 1 and a translation of the ovalbumin coding region is shown in FIG. 2. The amino acid sequence of a polypeptide (oval-f) derived from chick ovalbumin, but lacking any phenylalanine residues, is shown in FIG. 3. To optimize expression of this gene when expressed in *S. cerevisiae* the polypeptide sequence was 'backtranslated' using the most preferred pattern of codon usage for *S. cerevisiae* (FIG. 5). A derivative of chick ovalbumin was also designed in which the phenylalanine residues are replaced by tyrosine residues in order to attempt to produce a protein which has as near as possible the tertiary structure of chick ovalbumin. The amino acid sequence of the polypeptide (Yoval-f) and its corresponding gene produced as for the oval-f gene are shown in FIGS. 4 and 6 respectively. To further facilitate expression, cloning procedures and protein purification the following modifications were made to the basic gene.

1. Addition of a sequence corresponding to the 3' end of the mRNA from the end of the coding region to the poly A site, in order to enhance expression.

2. Addition of an extra TAA stop codon at the end of the gene, in order to ensure that no translation would take place beyond the normal coding region.

3. In order to assist in vitro manipulation, addition at either end of the synthetic gene of polylinkers which contained restriction sites for PstI, BamHI, SmaI, EcoRI and HindIII. The synthetic genes do not contain sites for these restriction enzymes. The polylinkers have the following sequence:

5' CTGCAGGATCCCGGGAATTCAAGCTT 3' (SEQ ID NO:43)

[PstI] [SmaI] [HindIII] [BamHI] [EcoRI]

4. In some versions of the synthetic gene a sequence corresponding to 6 histidine residues was added immediately downstream of the initiating methionine, in order to facilitate purification of the protein by a form of affinity chromatography.

Thus 4 basic variations on the original synthetic gene were obtained, with the following structures:

The synthetic gene is constructed via the synthesis of oligonucleotides each approximately 100 nucleotides long and designed in such a way that they overlap each other and will self-assemble by complementary base pairing into a contiguous structure which can be ligated via the appropriate sticky ends, generated by restriction endonuclease digestion into pEMBLyex4 or an appropriate *E. coli* vector such as pBR322 or pUC19. The sequences of the oligonucleotides and their arrangement is shown in FIG. 11. The end points of the individual oligonucleotides are marked by the character.

EXAMPLE 2

This example utilises bovine alpha-s1-casein. In this illustration only one synthetic gene was designed, but the general approach used in Example 1 can be applied to produce the other three genes analogous to those of Example 1, (i.e. those genes containing tyrosine replacements for phenylalanine and/or a run of six histidine residues immediately downstream of the N-terminal methionine).

The sequence of the mRNA for bovine alpha-s1-casein is shown in FIG. 12 and a translation of the region coding for the mature polypeptide is shown in FIG. 13. The modified form of the protein lacking phenylalanine residues and with an added N-terminal methionine (to permit translation) is shown in FIG. 14. A DNA sequence corresponding to this modified polypeptide produced using the most preferred pattern of codon usage for S. cerevisiae is shown in FIG. 15. Finally, the nucleotide sequence of the complete synthetic gene with the 3' untranslated region from the bovine alpha-s1-casein mRNA added on as well as the polylinkers (described in section A) is shown in FIG. 16. It should be noted that this particular synthetic gene has an internal EcoR1 site, as well as those present in the polylinkers and therefore EcoR1 should not be used in any in vitro manipulations of this gene during insertion into a vector.

EXAMPLE 3

This example concerns the construction of a bovine casein gene modified in that the codons for phenylalamine are replaced by codons for tyrosine.

Synthetic Gene Design

Eight C.100'mer oligonucleotides were designed, synthesised, and purified. These oligonucleotides (casein 1–8. see FIG. 16) formed the basis of two self-priming block assemblies in which the two blocks (designated A and B) overlapped by about 100 bp.

Following an initial round of PCR-mediated extension of the self-primed oligonucleotides as separate Blocks (A & B), a second round of PCR amplification using terminal flanking c. 20' mer primers (AL1 & AR1,BL1 & BR2; see FIG. 17 generated the two independent c.380 bp gene blocks A and B.

As mentioned above the design of the casein 1–8 c. 100' mer oligonucleotides was such that the encoded gene contained no phenylalanine codons, all these being substituted with tyrosine codons. A further feature was the incorporation of a number of unique restriction sites to facilitate in the final assembly of the whole gene from components of the two overlapping gene blocks. This duplication facilitates correction of erroneous PCR-mediated DNA synthesis.

Gene Block Synthesis

Using the 2-step PCR stategy described above both casein gene blocks A and B were amplified as discrete c. 380 bp products using Stratagene's native pfu DNA polymerase. Little success was achieved with the cloned enzyme. This particular enzyme was used because of its apparently superior fidelity properties.

Cloning and Sequencing of the Gene Blocks

Both blocks A & B were successfully cloned into Invitrogen's PCRII-TA cloning vector. Plasmid DNA was prepared from numerous isolates and these subjected to DNA sequence analysis using both universal and reverse sequencing primers. For the majority of clones full c. 380 bp reads were obtained. All these sequences were computer aligned against the "desired" sequence and against each other. Representative sample alignments for block A and B are shown in FIGS. 18a and b, and 19a and b, respectively.

PCRII-TA clones A100 and B69 were chosen as primary DNA sources. Two mutagenic c. 60' mer mutagenic oligo nucleotides, casein 9 and casein 10, were synthesised, purified, and used to amplify a "corrected" c.200 bp HpaI/HindIII C-terminus. This product was cloned into PCRII-TA vector and the sequence of several clones analysed using universal and reverse sequence primers. No perfect sequences were obtained but one clone (C20) which had only one base change, a G to T conversion resulting in a single amino acid change of trp to leu, was chosen.

The strategy taken was to assemble the gene sequence in pMTL22 by cloning the c. 200 bp hpa/HindIII C-terminal fragment of clone C20 next to the remainder of the gene derived from cloning of the c.265 bp BamHI/AatII of clone A100 and the c. 270 bp AatII/KpnI of clone B69. This has been achieved and the final nucleotide sequence verified yielding the "casein" gene sequence with a TTG triplet deletion at nt. pos. 258 and a G to T base change at nt. pos.

Cloning of the Casein Sequence into pMTL8133

The casein gene sequence was sub-cloned from the pMTL22 construct above into the "in house" E.coli/yeast expression vector pMTL8133. This vector is based on chloramphenicol resistance and has a hybrid PGK::REP 2 promoter element which has been shown to elicit high expression levels of other heterologous genes in both E.coli and Saccharomyces cerevisiae. The casein sequence was cloned as a PstI(flush-ended)/HindIII fragment into SspI/HindIII cleaved pMTL8133, such that it is correctly juxtaposed to the 5'-UTR sequence for elevated expression in yeast. The correct sequence at the cloning junction was verified by sequence analysis.

The modified gene has been clone into the E.coli/yeast expression vector pMTL8133 which has previously been shown to elicit expression of heterologous genes in both Escherichia coli and Sacharomyces cerevisiae.

Casein Expression Studies

E.coli strain INV alpha F' (endA1, recA1, hsdR17(r–k, m+k), supE44, λ-, thi-1, qyrA, relA1, φ80 lacZ ΔM15Δ (lacZYA-argF), deoR+, F genotype) has been transformed with the pMTL8133-casein recombinant plasmid and cultured in the presence of chloramphenicol (30 μg ml$^{-1}$) to maintain selection for the plasmid. Sonic extracts have been prepared from this culture and subjected to polyacrylamide gel electrophoresis alongside native bovine alpha casein (purchased from Sigma). Blotting of this gel onto nitrocellulose membrane followed by probing of the membrane sequentially with rabbit anti-casein and peroxidase-conjugated goat anti-rabbit antibody has revealed the presence of a polypeptide equal in size to the bovine alpha casein control. This polypeptide has a predicted molecular weight of 22 kDa. This protein product is detectable by means of antibody probing. No product is visible in coomassie blue stained polyacrylamide gels.

The pMTL8133-casein recombinant plasmid is used to transform a yeast (e.g. S.cerevisiae) in order to obtain expression of the modified casein encoded thereby.

If necessary or desirable, the base change at nt. pos. 512 can be corrected using a two-step strategy as follows. Firstly, the major part of the casein gene, 510 bp PstII/KpnI (nt. pos. 15 to 530) fragment is sub-cloned into PstI/KpnI cleaved pMTL20 with conomitant loss of AatII and NcoI polylinker sites. This enables the substitution of the c. 100 bp AatI/NcoI fragment containing the TTG triplet deletion with a correct sequence derived from the annealing of two complementary c. 100 bp oligonucleotides (nt. pos. 178 to 279). Such a clone is used for the second step involving mutagenic PCR using oligonucleotide primers AL2 and casein 15 whereby the base change at nt. pos. 512 is corrected.

---

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
      (A) LENGTH: 366 amino acids
      (B) TYPE: amino acid
      (D) TOPOLOGY: linear (ii) MOLECULE TYPE: protein (ix) FEATURE:
      (A) NAME/KEY: Protein
      (B) LOCATION: 1..366
      (D) OTHER INFORMATION: /note= "polypeptide derived from
         chicken ovalbumin lacking phenylalanine residues
         (oval-f)"

(xi) SEQUENCE DESCRIPTION: SEQ ID NO:1:

```
Met Gly Ser Ile Gly Ala Ala Ser Met Glu Cys Asp Val Lys Glu Leu
 1               5                  10                  15

Lys Val His His Ala Asn Glu Asn Ile Tyr Cys Pro Ile Ala Ile Met
                20                  25                  30

Ser Ala Leu Ala Met Val Tyr Leu Gly Ala Lys Asp Ser Thr Arg Thr
            35                  40                  45

Gln Ile Asn Lys Val Val Arg Asp Lys Leu Pro Gly Gly Asp Ser Ile
        50                  55                  60

Glu Ala Gln Cys Gly Thr Ser Val Asn Val His Ser Ser Leu Arg Asp
65                  70                  75                  80

Ile Leu Asn Gln Ile Thr Lys Pro Asn Asp Val Tyr Ser Ser Leu Ala
                85                  90                  95

Ser Arg Leu Tyr Ala Glu Glu Arg Tyr Pro Ile Leu Pro Glu Tyr Leu
            100                 105                 110

Gln Cys Val Lys Glu Leu Tyr Arg Gly Gly Leu Glu Pro Ile Asn Gln
        115                 120                 125

Thr Ala Ala Asp Gln Ala Arg Glu Leu Ile Asn Ser Trp Val Glu Ser
        130                 135                 140

Gln Thr Asn Gly Ile Ile Arg Asn Val Leu Gln Pro Ser Ser Val Asp
145                 150                 155                 160

Ser Gln Thr Ala Met Val Leu Val Asn Ala Ile Val Lys Gly Leu Trp
                165                 170                 175

Glu Lys Thr Lys Asp Glu Asp Thr Gln Ala Met Pro Arg Val Thr Glu
            180                 185                 190

Gln Glu Ser Lys Pro Val Gln Met Met Tyr Gln Ile Gly Leu Arg Val
        195                 200                 205

Ala Ser Met Ala Ser Glu Lys Met Lys Ile Leu Glu Leu Pro Ala Ser
        210                 215                 220

Gly Thr Met Ser Met Leu Val Leu Pro Asp Glu Val Ser Gly Leu
225                 230                 235                 240

Glu Gln Leu Glu Ser Ile Ile Asn Glu Lys Leu Thr Glu Trp Thr Ser
```

```
                    245                 250                 255
Ser Asn Val Met Glu Glu Arg Lys Ile Lys Val Tyr Leu Pro Arg Met
                260                 265                 270

Lys Met Glu Glu Lys Tyr Asn Leu Thr Ser Val Leu Met Ala Met Gly
            275                 280                 285

Ile Thr Asp Val Ser Ser Ala Asn Leu Ser Gly Ile Ser Ser Ala
        290                 295                 300

Glu Ser Leu Lys Ile Ser Gln Ala Val His Ala Ala His Ala Glu Ile
305                 310                 315                 320

Asn Glu Ala Gly Arg Glu Val Val Gly Ser Ala Glu Ala Gly Val Asp
                325                 330                 335

Ala Ala Ser Val Ser Glu Glu Arg Ala Asp His Pro Leu Cys Ile Lys
                340                 345                 350

His Ile Ala Thr Asn Ala Val Leu Gly Arg Cys Val Ser Pro
            355                 360                 365

(2) INFORMATION FOR SEQ ID NO:2:

(i) SEQUENCE CHARACTERISTICS:
        (A) LENGTH: 386 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..386
        (D) OTHER INFORMATION: /note= "polypeptide derived from
            chicken ovalbumin in which phenylalanine residues
            have been replaced by tyrosine residues (Yoval-f)"

(xi) SEQUENCE DESCRIPTION: SEQ ID NO:2:

Met Gly Ser Ile Gly Ala Ala Ser Met Glu Tyr Cys Tyr Asp Val Tyr
1               5                   10                  15

Lys Glu Leu Lys Val His His Ala Asn Glu Asn Ile Tyr Tyr Cys Pro
            20                  25                  30

Ile Ala Ile Met Ser Ala Leu Ala Met Val Tyr Leu Gly Ala Lys Asp
        35                  40                  45

Ser Thr Arg Thr Gln Ile Asn Lys Val Val Arg Tyr Asp Lys Leu Pro
    50                  55                  60

Gly Tyr Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
            85                  90                  95

Val Tyr Ser Tyr Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
            115                 120                 125

Gly Leu Glu Pro Ile Asn Tyr Gln Thr Ala Ala Asp Gln Ala Arg Glu
130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Tyr Lys Gly Leu Trp Glu Lys Thr Tyr Lys Asp Glu
            180                 185                 190

Asp Thr Gln Ala Met Pro Tyr Arg Val Thr Glu Gln Glu Ser Lys Pro
```

```
                195                 200                 205
Val Gln Met Met Tyr Gln Ile Gly Leu Tyr Arg Val Ala Ser Met Ala
    210                 215                 220

Ser Glu Lys Met Lys Ile Leu Glu Leu Pro Tyr Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Tyr Glu Lys Leu Thr Glu Trp Thr Ser Ser Asn
                260                 265                 270

Val Met Glu Glu Arg Lys Ile Lys Val Tyr Leu Pro Arg Met Lys Met
            275                 280                 285

Glu Glu Lys Tyr Asn Leu Thr Ser Val Leu Met Ala Met Gly Ile Thr
    290                 295                 300

Asp Val Tyr Ser Ser Ser Ala Asn Leu Ser Gly Ile Ser Ser Ala Glu
305                 310                 315                 320

Ser Leu Lys Ile Ser Gln Ala Val His Ala Ala His Ala Glu Ile Asn
                325                 330                 335

Glu Ala Gly Arg Glu Val Val Gly Ser Ala Glu Ala Gly Val Asp Ala
            340                 345                 350

Ala Ser Val Ser Glu Glu Tyr Arg Ala Asp His Pro Tyr Leu Tyr Cys
            355                 360                 365

Ile Lys His Ile Ala Thr Asn Ala Val Leu Tyr Tyr Gly Arg Cys Val
    370                 375                 380

Ser Pro
385
```

(2) INFORMATION FOR SEQ ID NO:3:

(i) SEQUENCE CHARACTERISTICS:
        (A) LENGTH: 1098 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1098
        (D) OTHER INFORMATION: /product= "oval-f"
            /note="synthetic gene encoding
            derivative of chicken ovalbumin lacking
            phenylalanine using optimal pattern of
            codon usage for S. cerevisiae"

(xi) SEQUENCE DESCRIPTION: SEQ ID NO:3:

```
ATGGGTTCTA TTGGTGCTGC TTCTATGGAA TGTGATGTTA AGAATTGAA AGTTCATCAT     60

GCTAATGAAA ATATTTATTG TCCAATTGCT ATTATGTCTG CTTTGGCTAT GGTTTATTTG   120

GGTGCTAAAG ATTCTACTAG AACTCAAATT AATAAAGTTG TTAGAGATAA ATTGCCAGGT   180

GGTGATTCTA TTGAAGCTCA ATGTGGTACT TCTGTTAATG TTCATTCTTC TTTGAGAGAT   240

ATTTTGAATC AAATTACTAA ACCAAATGAT GTTTATTCTT CTTTGGCTTC TAGATTGTAT   300

GCTGAAGAAA GATATCCAAT TTTGCCAGAA TATTTGCAAT GTGTTAAAGA ATTGTATAGA   360

GGTGGTTTGG AACCAATTAA TCAAACTGCT GCTGATCAAG CTAGAGAATT GATTAATTCT   420

TGGGTTGAAT CTCAAACTAA TGGTATTATT AGAAATGTTT TGCAACCATC TTCTGTTGAT   480

TCTCAAACTG CTATGGTTTT GGTTAATGCT ATTGTTAAAG GTTTGTGGGA AAAAACTAAA   540

GATGAAGATA CTCAAGCTAT GCCAAGAGTT ACTGAACAAG AATCTAAACC AGTTCAAATG   600
```

-continued

```
ATGTATCAAA TTGGTTTGAG AGTTGCTTCT ATGGCTTCTG AAAAAATGAA AATTTTGGAA    660

TTGCCAGCTT CTGGTACTAT GTCTATGTTG GTTTTGTTGC CAGATGAAGT TTCTGGTTTG    720

GAACAATTGG AATCTATTAT TAATGAAAAA TTGACTGAAT GGACTTCTTC TAATGTTATG    780

GAAGAAAGAA AAATTAAAGT TTATTTGCCA AGAATGAAAA TGGAAGAAAA ATATAATTTG    840

ACTTCTGTTT TGATGGCTAT GGGTATTACT GATGTTTCTT CTTCTGCTAA TTTGTCTGGT    900

ATTTCTTCTG CTGAATCTTT GAAAATTTCT CAAGCTGTTC ATGCTGCTCA TGCTGAAATT    960

AATGAAGCTG GTAGAGAAGT TGTTGGTTCT GCTGAAGCTG GTGTTGATGC TGCTTCTGTT   1020

TCTGAAGAAA GAGCTGATCA TCCATTGTGT ATTAAACATA TTGCTACTAA TGCTGTTTTG   1080

GGTAGATGTG TTTCTCCA                                                 1098
```

(2) INFORMATION FOR SEQ ID NO:4:

(i) SEQUENCE CHARACTERISTICS:
        (A) LENGTH: 1158 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1158
        (D) OTHER INFORMATION: /product= "Yoval-f"
            /note "synthetic gene encoding
            derivative of chicken ovalbumin in which
            phenylalanines are replaced by tyrosines
            using optimal pattern of codon usage for
            S. cerevisiae"

(xi) SEQUENCE DESCRIPTION: SEQ ID NO:4:

```
ATGGGTTCTA TTGGTGCTGC TTCTATGGAA TATTGTTATG ATGTTTATAA AGAATTGAAA     60

GTTCATCATG CTAATGAAAA TATTTATTAT TGTCCAATTG CTATTATGTC TGCTTTGGCT    120

ATGGTTTATT TGGGTGCTAA AGATTCTACT AGAACTCAAA TTAATAAAGT TGTTAGATAT    180

GATAAATTGC CAGGTTATGG TGATTCTATT GAAGCTCAAT GTGGTACTTC TGTTAATGTT    240

CATTCTTCTT TGAGAGATAT TTTGAATCAA ATTACTAAAC CAAATGATGT TTATTCTTAT    300

TCTTTGGCTT CTAGATTGTA TGCTGAAGAA AGATATCCAA TTTTGCCAGA ATATTTGCAA    360

TGTGTTAAAG AATTGTATAG AGGTGGTTTG GAACCAATTA ATTATCAAAC TGCTGCTGAT    420

CAAGCTAGAG AATTGATTAA TTCTTGGGTT GAATCTCAAA CTAATGGTAT TATTAGAAAT    480

GTTTTGCAAC CATCTTCTGT TGATTCTCAA ACTGCTATGG TTTTGGTTAA TGCTATTGTT    540

TATAAAGGTT TGTGGGAAAA AACTTATAAA GATGAAGATA CTCAAGCTAT GCCATATAGA    600

GTTACTGAAC AAGAATCTAA ACCAGTTCAA ATGATGTATC AAATTGGTTT GTATAGAGTT    660

GCTTCTATGG CTTCTGAAAA AATGAAAATT TTGGAATTGC CATATGCTTC TGGTACTATG    720

TCTATGTTGG TTTTGTTGCC AGATGAAGTT TCTGGTTTGG AACAATTGGA ATCTATTATT    780

AATTATGAAA AATTGACTGA ATGGACTTCT TCTAATGTTA TGGAAGAAAG AAAAATTAAA    840

GTTTATTTGC CAAGAATGAA AATGGAAGAA AAATATAATT TGACTTCTGT TTTGATGGCT    900

ATGGGTATTA CTGATGTTTA TTCTTCTTCT GCTAATTTGT CTGGTATTTC TTCTGCTGAA    960

TCTTTGAAAA TTTCTCAAGC TGTTCATGCT GCTCATGCTG AAATTAATGA AGCTGGTAGA   1020

GAAGTTGTTG GTTCTGCTGA AGCTGGTGTT GATGCTGCTT CTGTTTCTGA AGAATATAGA   1080

GCTGATCATC CATATTTGTA TTGTATTAAA CATATTGCTA CTAATGCTGT TTTGTATTAT   1140
```

```
GGTAGATGTG TTTCTCCA                                                      1158
```

(2) INFORMATION FOR SEQ ID NO:5:

(i) SEQUENCE CHARACTERISTICS:
        (A) LENGTH: 1803 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1803
        (D) OTHER INFORMATION: /note "construct pl+oval-f+3end"

(xi) SEQUENCE DESCRIPTION: SEQ ID NO:5:

```
CTGCAGGATC CCGGGAATTC AAGCTTATGG GTTCTATTGG TGCTGCTTCT ATGGAATGTG     60

ATGTTAAAGA ATTGAAAGTT CATCATGCTA ATGAAAATAT TTATTGTCCA ATTGCTATTA    120

TGTCTGCTTT GGCTATGGTT TATTTGGGTG CTAAAGATTC TACTAGAACT CAAATTAATA    180

AAGTTGTTAG AGATAAATTG CCAGGTGGTG ATTCTATTGA AGCTCAATGT GGTACTTCTG    240

TTAATGTTCA TTCTTCTTTG AGAGATATTT TGAATCAAAT TACTAAACCA AATGATGTTT    300

ATTCTTCTTT GGCTTCTAGA TTGTATGCTG AAGAAAGATA TCCAATTTTG CCAGAATATT    360

TGCAATGTGT TAAAGAATTG TATAGAGGTG GTTTGGAACC AATTAATCAA ACTGCTGCTG    420

ATCAAGCTAG AGAATTGATT AATTCTTGGG TTGAATCTCA AACTAATGGT ATTATTAGAA    480

ATGTTTTGCA ACCATCTTCT GTTGATTCTC AAACTGCTAT GGTTTTGGTT AATGCTATTG    540

TTAAAGGTTT GTGGGAAAAA ACTAAAGATG AAGATACTCA AGCTATGCCA AGAGTTACTG    600

AACAAGAATC TAAACCAGTT CAAATGATGT ATCAAATTGG TTTGAGAGTT GCTTCTATGG    660

CTTCTGAAAA AATGAAAATT TGGAATTGC CAGCTTCTGG TACTATGTCT ATGTTGGTTT    720

TGTTGCCAGA TGAAGTTTCT GGTTTGGAAC AATTGGAATC TATTATTAAT GAAAAATTGA    780

CTGAATGGAC TTCTTCTAAT GTTATGGAAG AAAGAAAAAT TAAAGTTTAT TTGCCAAGAA    840

TGAAAATGGA AGAAAAATAT AATTTGACTT CTGTTTTGAT GGCTATGGGT ATTACTGATG    900

TTTCTTCTTC TGCTAATTTG TCTGGTATTT CTTCTGCTGA ATCTTTGAAA ATTTCTCAAG    960

CTGTTCATGC TGCTCATGCT GAAATTAATG AAGCTGGTAG AGAAGTTGTT GGTTCTGCTG   1020

AAGCTGGTGT TGATGCTGCT TCTGTTTCTG AAGAAAGAGC TGATCATCCA TTGTGTATTA   1080

AACATATTGC TACTAATGCT GTTTTGGGTA GATGTGTTTC TCCATAATAA AAAGAAGAAA   1140

GCTGAAAAAC TCTGTCCCTT CCAACAAGAC CCAGAGCACT GTAGTATCAG GGGTAAAATG   1200

AAAAGTATGT TCTCTGCTGC ATCCAGACTT CATAAAAGCT GGAGCTTAAT CTAGAAAAAA   1260

AATCAGAAAG AAATTACACT GTGAGAACAG GTGCAATTCA CTTTTCCTTT ACACAGAGTA   1320

ATACTGGTAA CTCATGGATG AAGGCTTAAG GGAATGAAAT TGGACTCACA GTACTGAGTC   1380

ATCACACTGA AAAATGCAAC CTGATACATC AGCAGAAGGT TTATGGGGGA AAAATGCAGC   1440

CTTCCAATTA AGCCAGATAT CTGTATGACC AAGCTGCTCC AGAATTAGTC ACTCAAAATC   1500

TCTCAGATTA AATTATCAAC TGTCACCAAC CATTCCTATG CTGACAAGGC AATTGCTTGT   1560

TCTCTGTGTT CCTGATACTA CAAGGCTCTT CCTGACTTCC TAAAGATGCA TTATAAAAAT   1620

CTTATAATTC ACATTTCTCC CTAAACTTTG ACTCAATCAT GGTATGTTGG CAAATATGGT   1680

ATATTACTAT TCAAATTGTT TTCCTTGTAC CCATATGTAA TGGGTCTTGT GAATGTGCTC   1740
```

```
TTTTGTTCCT TTAATCATAA TAAAAACATG TTTAAGCCTG CAGGATCCCG GGAATTCAAG    1800

CTT                                                                 1803
```

(2) INFORMATION FOR SEQ ID NO:6:

(i) SEQUENCE CHARACTERISTICS:
        (A) LENGTH: 1821 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1821
        (D) OTHER INFORMATION: /note "construct pl+h6oval-f+3end"

(xi) SEQUENCE DESCRIPTION: SEQ ID NO:6:

```
CTGCAGGATC CCGGGAATTC AAGCTTATGC ATCATCATCA TCATCATGGT TCTATTGGTG      60

CTGCTTCTAT GGAATGTGAT GTTAAAGAAT TGAAAGTTCA TCATGCTAAT GAAAATATTT     120

ATTGTCCAAT TGCTATTATG TCTGCTTTGG CTATGGTTTA TTTGGGTGCT AAAGATTCTA     180

CTAGAACTCA AATTAATAAA GTTGTTAGAG ATAAATTGCC AGGTGGTGAT TCTATTGAAG     240

CTCAATGTGG TACTTCTGTT AATGTTCATT CTTCTTTGAG AGATATTTTG AATCAAATTA     300

CTAAACCAAA TGATGTTTAT TCTTCTTTGG CTTCTAGATT GTATGCTGAA GAAAGATATC     360

CAATTTTGCC AGAATATTTG CAATGTGTTA AGAATTGTA TAGAGGTGGT TTGGAACCAA      420

TTAATCAAAC TGCTGCTGAT CAAGCTAGAG AATTGATTAA TTCTTGGGTT GAATCTCAAA     480

CTAATGGTAT TATTAGAAAT GTTTTGCAAC CATCTTCTGT TGATTCTCAA ACTGCTATGG     540

TTTTGGTTAA TGCTATTGTT AAAGGTTTGT GGGAAAAAAC TAAAGATGAA GATACTCAAG     600

CTATGCCAAG AGTTACTGAA CAAGAATCTA AACCAGTTCA AATGATGTAT CAAATTGGTT     660

TGAGAGTTGC TTCTATGGCT TCTGAAAAAA TGAAAATTTT GGAATTGCCA GCTTCTGGTA     720

CTATGTCTAT GTTGGTTTTG TTGCCAGATG AAGTTTCTGG TTTGGAACAA TTGGAATCTA     780

TTATTAATGA AAAATTGACT GAATGGACTT CTTCTAATGT TATGGAAGAA AGAAAAATTA     840

AAGTTTATTT GCCAAGAATG AAAATGGAAG AAAAATATAA TTTGACTTCT GTTTTGATGG     900

CTATGGGTAT TACTGATGTT TCTTCTTCTG CTAATTTGTC TGGTATTTCT TCTGCTGAAT     960

CTTTGAAAAT TTCTCAAGCT GTTCATGCTG CTCATGCTGA AATTAATGAA GCTGGTAGAG    1020

AAGTTGTTGG TTCTGCTGAA GCTGGTGTTG ATGCTGCTTC TGTTTCTGAA GAAAGAGCTG    1080

ATCATCCATT GTGTATTAAA CATATTGCTA CTAATGCTGT TTTGGGTAGA TGTGTTTCTC    1140

CATAATAAAA AGAAGAAAGC TGAAAAACTC TGTCCCTTCC AACAAGACCC AGAGCACTGT    1200

AGTATCAGGG GTAAAATGAA AAGTATGTTC TCTGCTGCAT CCAGACTTCA TAAAAGCTGG    1260

AGCTTAATCT AGAAAAAAAA TCAGAAAGAA ATTACACTGT GAGAACAGGT GCAATTCACT    1320

TTTCCTTTAC ACAGAGTAAT ACTGGTAACT CATGGATGAA GGCTTAAGGG AATGAAATTG    1380

GACTCACAGT ACTGAGTCAT CACACTGAAA AATGCAACCT GATACATCAG CAGAAGGTTT    1440

ATGGGGAAA AATGCAGCCT TCCAATTAAG CCAGATATCT GTATGACCAA GCTGCTCCAG    1500

AATTAGTCAC TCAAAATCTC TCAGATTAAA TTATCAACTG TCACCAACCA TTCCTATGCT    1560

GACAAGGCAA TTGCTTGTTC TCTGTGTTCC TGATACTACA AGGCTCTTCC TGACTTCCTA    1620

AAGATGCATT ATAAAAATCT TATAATTCAC ATTTCTCCCT AAACTTTGAC TCAATCATGG    1680

TATGTTGGCA AATATGGTAT ATTACTATTC AAATTGTTTT CCTTGTACCC ATATGTAATG    1740
```

```
GGTCTTGTGA ATGTGCTCTT TTGTTCCTTT AATCATAATA AAAACATGTT TAAGCCTGCA      1800

GGATCCCGGG AATTCAAGCT T                                                1821
```

(2) INFORMATION FOR SEQ ID NO:7:

(i) SEQUENCE CHARACTERISTICS:
        (A) LENGTH: 1863 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1863
        (D) OTHER INFORMATION: /note "construct p1+Yoval-f+3end"

(xi) SEQUENCE DESCRIPTION: SEQ ID NO:7:

```
CTGCAGGATC CCGGGAATTC AAGCTTATGG GTTCTATTGG TGCTGCTTCT ATGGAATATT        60

GTTATGATGT TTATAAAGAA TTGAAAGTTC ATCATGCTAA TGAAAATATT TATTATTGTC       120

CAATTGCTAT TATGTCTGCT TTGGCTATGG TTTATTTGGG TGCTAAAGAT TCTACTAGAA       180

CTCAAATTAA TAAAGTTGTT AGATATGATA AATTGCCAGG TTATGGTGAT TCTATTGAAG       240

CTCAATGTGG TACTTCTGTT AATGTTCATT CTTCTTTGAG AGATATTTTG AATCAAATTA       300

CTAAACCAAA TGATGTTTAT TCTTATTCTT TGGCTTCTAG ATTGTATGCT GAAGAAAGAT       360

ATCCAATTTT GCCAGAATAT TTGCAATGTG TTAAAGAATT GTATAGAGGT GGTTTGGAAC       420

CAATTAATTA TCAAACTGCT GCTGATCAAG CTAGAGAATT GATTAATTCT TGGGTTGAAT       480

CTCAAACTAA TGGTATTATT AGAAATGTTT TGCAACCATC TTCTGTTGAT CTCAAACTG        540

CTATGGTTTT GGTTAATGCT ATTGTTTATA AAGGTTTGTG GGAAAAAACT TATAAAGATG       600

AAGATACTCA AGCTATGCCA TATAGAGTTA CTGAACAAGA ATCTAAACCA GTTCAAATGA       660

TGTATCAAAT TGGTTTGTAT AGAGTTGCTT CTATGGCTTC TGAAAAAATG AAAATTTTGG       720

AATTGCCATA TGCTTCTGGT ACTATGTCTA TGTTGGTTTT GTTGCCAGAT GAAGTTTCTG       780

GTTTGGAACA ATTGGAATCT ATTATTAATT ATGAAAAATT GACTGAATGG ACTTCTTCTA       840

ATGTTATGGA AGAAAGAAAA ATTAAAGTTT ATTTGCCAAG AATGAAAATG GAAGAAAAAT       900

ATAATTTGAC TTCTGTTTTG ATGGCTATGG GTATTACTGA TGTTTATTCT TCTTCTGCTA       960

ATTTGTCTGG TATTTCTTCT GCTGAATCTT TGAAAATTTC TCAAGCTGTT CATGCTGCTC      1020

ATGCTGAAAT TAATGAAGCT GGTAGAGAAG TTGTTGGTTC TGCTGAAGCT GGTGTTGATG      1080

CTGCTTCTGT TTCTGAAGAA TATAGAGCTG ATCATCCATA TTTGTATTGT ATTAAACATA      1140

TTGCTACTAA TGCTGTTTTG TATTATGGTA GATGTGTTTC TCCATAATAA AAGAAGAAA       1200

GCTGAAAAAC TCTGTCCCTT CCAACAAGAC CCAGAGCACT GTAGTATCAG GGTAAAATG       1260

AAAAGTATGT TCTCTGCTGC ATCCAGACTT CATAAAAGCT GGAGCTTAAT CTAGAAAAAA      1320

AATCAGAAAG AAATTACACT GTGAGAACAG GTGCAATTCA CTTTTCCTTT ACACAGAGTA      1380

ATACTGGTAA CTCATGGATG AAGGCTTAAG GGAATGAAAT TGGACTCACA GTACTGAGTC      1440

ATCACACTGA AAAATGCAAC CTGATACATC AGCAGAAGGT TTATGGGGGA AAAATGCAGC      1500

CTTCCAATTA AGCCAGATAT CTGTATGACC AAGCTGCTCC AGAATTAGTC ACTCAAAATC      1560

TCTCAGATTA AATTATCAAC TGTCACCAAC CATTCCTATG CTGACAAGGC AATTGCTTGT      1620

TCTCTGTGTT CCTGATACTA CAAGGCTCTT CCTGACTTCC TAAAGATGCA TTATAAAAAT      1680
```

```
CTTATAATTC ACATTTCTCC CTAAACTTTG ACTCAATCAT GGTATGTTGG CAAATATGGT      1740

ATATTACTAT TCAAATTGTT TTCCTTGTAC CCATATGTAA TGGGTCTTGT GAATGTGCTC      1800

TTTTGTTCCT TTAATCATAA TAAAAACATG TTTAAGCCTG CAGGATCCCG GGAATTCAAG      1860

CTT                                                                    1863
```

(2) INFORMATION FOR SEQ ID NO:8:

(i) SEQUENCE CHARACTERISTICS:
        (A) LENGTH: 1881 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1881
        (D) OTHER INFORMATION: /note "construct pl+h6Yoval-f+3end"

(xi) SEQUENCE DESCRIPTION: SEQ ID NO:8:

```
CTGCAGGATC CCGGGAATTC AAGCTTATGC ATCATCATCA TCATCATGGT TCTATTGGTG        60

CTGCTTCTAT GGAATATTGT TATGATGTTT ATAAAGAATT GAAAGTTCAT CATGCTAATG       120

AAAATATTTA TTATTGTCCA ATTGCTATTA TGTCTGCTTT GGCTATGGTT TATTTGGGTG       180

CTAAAGATTC TACTAGAACT CAAATTAATA AGTTGTTAG ATATGATAAA TTGCCAGGTT        240

ATGGTGATTC TATTGAAGCT CAATGTGGTA CTTCTGTTAA TGTTCATTCT TCTTTGAGAG       300

ATATTTTGAA TCAAATTACT AAACCAAATG ATGTTTATTC TTATTCTTTG GCTTCTAGAT       360

TGTATGCTGA AGAAAGATAT CCAATTTTGC CAGAATATTT GCAATGTGTT AAAGAATTGT       420

ATAGAGGTGG TTTGGAACCA ATTAATTATC AAACTGCTGC TGATCAAGCT AGAGAATTGA       480

TTAATTCTTG GGTTGAATCT CAAACTAATG GTATTATTAG AAATGTTTTG CAACCATCTT       540

CTGTTGATTC TCAAACTGCT ATGGTTTTGG TTAATGCTAT TGTTTATAAA GGTTTGTGGG       600

AAAAAACTTA TAAAGATGAA GATACTCAAG CTATGCCATA TAGAGTTACT GAACAAGAAT       660

CTAAACCAGT TCAAATGATG TATCAAATTG GTTTGTATAG AGTTGCTTCT ATGGCTTCTG       720

AAAAAATGAA AATTTTGGAA TTGCCATATG CTTCTGGTAC TATGTCTATG TTGGTTTTGT       780

TGCCAGATGA AGTTTCTGGT TTGGAACAAT TGGAATCTAT TATTAATTAT GAAAAATTGA       840

CTGAATGGAC TTCTTCTAAT GTTATGGAAG AAAGAAAAAT TAAAGTTTAT TTGCCAAGAA       900

TGAAAATGGA AGAAAAATAT AATTTGACTT CTGTTTTGAT GGCTATGGGT ATTACTGATG       960

TTTATTCTTC TTCTGCTAAT TTGTCTGGTA TTTCTTCTGC TGAATCTTTG AAAATTTCTC      1020

AAGCTGTTCA TGCTGCTCAT GCTGAAATTA ATGAAGCTGG TAGAGAAGTT GTTGGTTCTG      1080

CTGAAGCTGG TGTTGATGCT GCTTCTGTTT CTGAAGAATA TAGAGCTGAT CATCCATATT      1140

TGTATTGTAT TAAACATATT GCTACTAATG CTGTTTTGTA TTATGGTAGA TGTGTTTCTC      1200

CATAATAAAA AGAAGAAAGC TGAAAAACTC TGTCCCTTCC AACAAGACCC AGAGCACTGT      1260

AGTATCAGGG GTAAAATGAA AAGTATGTTC TCTGCTGCAT CCAGACTTCA TAAAAGCTGG      1320

AGCTTAATCT AGAAAAAAAA TCAGAAAGAA ATTACACTGT GAGAACAGGT GCAATTCACT      1380

TTTCCTTTAC ACAGAGTAAT ACTGGTAACT CATGGATGAA GGCTTAAGGG AATGAAATTG      1440

GACTCACAGT ACTGAGTCAT CACACTGAAA AATGCAACCT GATACATCAG CAGAAGGTTT      1500

ATGGGGAAA AATGCAGCCT TCCAATTAAG CCAGATATCT GTATGACCAA GCTGCTCCAG      1560

AATTAGTCAC TCAAAATCTC TCAGATTAAA TTATCAACTG TCACCAACCA TTCCTATGCT      1620
```

-continued

```
GACAAGGCAA TTGCTTGTTC TCTGTGTTCC TGATACTACA AGGCTCTTCC TGACTTCCTA    1680

AAGATGCATT ATAAAAATCT TATAATTCAC ATTTCTCCCT AAACTTTGAC TCAATCATGG    1740

TATGTTGGCA AATATGGTAT ATTACTATTC AAATTGTTTT CCTTGTACCC ATATGTAATG    1800

GGTCTTGTGA ATGTGCTCTT TTGTTCCTTT AATCATAATA AAAACATGTT TAAGCCTGCA    1860

GGATCCCGGG AATTCAAGCT T                                             1881
```

(2) INFORMATION FOR SEQ ID NO:9:

(i) SEQUENCE CHARACTERISTICS:
      (A) LENGTH: 192 amino acids
      (B) TYPE: amino acid
      (D) TOPOLOGY: linear (ii) MOLECULE TYPE: protein (ix) FEATURE:
      (A) NAME/KEY: Protein
      (B) LOCATION: 1..192
      (D) OTHER INFORMATION: /note= "mature bovine alpha-s1-casein
          with phenylalanine residues removed and
          addition of an N-terminal methionine
          residue"

(xi) SEQUENCE DESCRIPTION: SEQ ID NO:9:

```
Met Arg Pro Lys His Pro Ile Lys His Gln Gly Leu Pro Gln Glu Val
1               5                   10                  15

Leu Asn Glu Asn Leu Leu Arg Val Ala Pro Pro Glu Val Gly Lys Glu
                20                  25                  30

Lys Val Asn Glu Leu Ser Lys Asp Ile Gly Ser Glu Ser Thr Glu Asp
            35                  40                  45

Gln Ala Met Glu Asp Ile Lys Gln Met Glu Ala Glu Ser Ile Ser Ser
        50                  55                  60

Ser Glu Glu Ile Val Pro Asn Ser Val Glu Gln Lys His Ile Gln Lys
65                  70                  75                  80

Glu Asp Val Pro Ser Glu Arg Tyr Leu Gly Tyr Leu Glu Gln Leu Leu
                85                  90                  95

Arg Leu Lys Lys Tyr Lys Val Pro Gln Leu Glu Ile Val Pro Asn Ser
                100                 105                 110

Ala Glu Glu Arg Leu His Ser Met Lys Glu Gly Ile His Ala Gln Gln
            115                 120                 125

Lys Glu Pro Met Ile Gly Val Asn Gln Glu Leu Ala Tyr Tyr Pro Glu
        130                 135                 140

Leu Arg Gln Tyr Gln Leu Asp Ala Tyr Pro Ser Gly Ala Trp Tyr Tyr
145                 150                 155                 160

Val Pro Leu Gly Thr Gln Tyr Thr Asp Ala Pro Ser Ser Asp Ile Pro
                165                 170                 175

Asn Pro Ile Gly Ser Glu Asn Ser Glu Lys Thr Thr Met Pro Leu Trp
                180                 185                 190
```

(2) INFORMATION FOR SEQ ID NO:10:

(i) SEQUENCE CHARACTERISTICS:
      (A) LENGTH: 582 base pairs
      (B) TYPE: nucleic acid
      (C) STRANDEDNESS: single
      (D) TOPOLOGY: linear (ii) MOLECULE TYPE: DNA (ix) FEATURE:

(A) NAME/KEY: -
(B) LOCATION: 1..582
(D) OTHER INFORMATION: /note= "synthetic gene encoding
    derivative of mature bovine
    alpha-s1-casein lacking phenylalanine
    residues, addition of an N-terminal
    methionine residue and two stop codons
    at the end of the casein coding
    sequence, using optimal pattern of
    codon usage for S. cerevisiae"

(xi) SEQUENCE DESCRIPTION: SEQ ID NO:10:

```
ATGAGACCAA AACATCCAAT TAAACATCAA GGTTTGCCAC AAGAAGTTTT GAATGAAAAT      60

TTGTTGAGAG TTGCTCCACC AGAAGTTGGT AAAGAAAAAG TTAATGAATT GTCTAAAGAT     120

ATTGGTTCTG AATCTACTGA AGATCAAGCT ATGGAAGATA TTAAACAAAT GGAAGCTGAA     180

TCTATTTCTT CTTCTGAAGA ATTGTTCCA AATTCTGTTG AACAAAAACA TATTCAAAAA      240

GAAGATGTTC CATCTGAAAG ATATTTGGGT TATTTGGAAC AATTGTTGAG ATTGAAAAAA     300

TATAAAGTTC CACAATTGGA AATTGTTCCA AATTCTGCTG AAGAAAGATT GCATTCTATG     360

AAAGAAGGTA TTCATGCTCA ACAAAAAGAA CCAATGATTG GTGTTAATCA AGAATTGGCT     420

TATTATCCAG AATTGAGACA ATATCAATTG GATGCTTATC CATCTGGTGC TTGGTATTAT     480

GTTCCATTGG GTACTCAATA TACTGATGCT CCATCTTCTG ATATTCCAAA TCCAATTGGT     540

TCTGAAAATT CTGAAAAAAC TACTATGCCA TTGTGGTGAT GA                        582
```

(2) INFORMATION FOR SEQ ID NO:11:

(i) SEQUENCE CHARACTERISTICS:
       (A) LENGTH: 1056 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: -
       (B) LOCATION: 1..1056
       (D) OTHER INFORMATION: /note= "synthetic gene encoding
           derivative of mature bovine
           alpha-s1-casein lacking phenylalanine
           residues, addition of an N-terminal
           methionine residue, two stop codons
           at the end of the casein coding sequence
           and the non-translated 3' region of
           bovine alpha-s1-casein mRNA, using
           optimal pattern of codon usage for
           S. cerevisiae"

(xi) SEQUENCE DESCRIPTION: SEQ ID NO:11:

```
CTGCAGGATC CCGGGAATTC TAGAAGCTTA TGAGACCAAA ACATCCAATT AAACATCAAG      60

GTTTGCCACA AGAAGTTTTG AATGAAAATT TGTTGAGAGT TGCTCCACCA GAAGTTGGTA     120

AAGAAAAAGT TAATGAATTG TCTAAAGATA TTGGTTCTGA ATCTACTGAA GATCAAGCTA     180

TGGAAGATAT TAAACAAATG GAAGCTGAAT CTATTTCTTC TTCTGAAGAA ATTGTTCCAA     240

ATTCTGTTGA ACAAAAACAT ATTCAAAAAG AAGATGTTCC ATCTGAAAGA TATTTGGGTT     300

ATTTGGAACA ATTGTTGAGA TTGAAAAAAT ATAAAGTTCC ACAATTGGAA ATTGTTCCAA     360

ATTCTGCTGA AGAAAGATTG CATTCTATGA AAGAAGGTAT TCATGCTCAA CAAAAAGAAC     420

CAATGATTGG TGTTAATCAA GAATTGGCTT ATTATCCAGA ATTGAGACAA TATCAATTGG     480

ATGCTTATCC ATCTGGTGCT TGGTATTATG TTCCATTGGG TACTCAATAT ACTGATGCTC     540

CATCTTCTGA TATTCCAAAT CCAATTGGTT CTGAAAATTC TGAAAAAACT ACTATGCCAT     600
```

```
TGTGGTGATG AAAGAGTCAA GTGAATTCTG AGGGACTCCA CAGTTATGGT CTTTGATGGG      660

TCTGAAAATT CCATGCTCTA CATGTCGCCT CATCTACATG TCAAACCATT CATCCAAAGG      720

CTTCAACTGC TGTTTTAGAA CAGGGCAATC TCAAACTGAG GCACTCCTTG ATGCTCTACT      780

GTATTTTAGA TAGTGTAACA TCCTTAAGTG AAATTGTCCT AACAGCTTGT TACCTAAATT      840

CCAGTAGTAT CATGCTGGTA TAAAGGCCAC TGAGTCAAAG GGAATTAAAG TCTTCATTAA      900

ATTTCTGTAT GGAAAATGTT TTAAAAGCCT TTGAATCACT TCTCCTGTAA GTGCCATCAT      960

ATCAAATAAT TGTGTGCATT AACTGAGATT TTGTCTTTCT TCTTTTCAAT AAATTACATT     1020

TTAAGGCCTG CAGGATCCCG GGAATTCTAG AAGCTT                               1056

(2) INFORMATION FOR SEQ ID NO:12:

(i) SEQUENCE CHARACTERISTICS:
        (A) LENGTH: 374 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..374
        (D) OTHER INFORMATION: /note= "predicted sequence of bovine
            casein block A"

(xi) SEQUENCE DESCRIPTION: SEQ ID NO:12:

AATCAGGATC CCGGGCATAT GAGACCAAAA CATCCAATTA AACATCAAGG TTTGCCACAA        60

GAAGTTTTGA ACGAAAACTT GTTGAGATAC TACGTTGCTC CATACCCAGA AGTTTACGGT       120

AAAGAAAAAG TTAATGAATT GTCTAAAGAT ATCGGTTCTG AATCTACTGA AGATCAAGCC       180

ATGGAAGATA TTAAACAAAT GGAAGCTGAA TCTATCTCTT CTTCTGAAGA AATCGTCCCA       240

AACTCTGTTG AACAAAAACA TATTCAAAAA GAAGACGTCC CATCTGAAAG ATACTTGGGT       300

TACTTAGAAC AATTGTTGAG ATTGAAAAAA TACAAAGTTC ACAATTGGA AATCGTCCCA        360

AACTCAGCTG AAGA                                                        374

(2) INFORMATION FOR SEQ ID NO:13:

(i) SEQUENCE CHARACTERISTICS:
        (A) LENGTH: 125 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..125
        (D) OTHER INFORMATION: /note= "predicted sequence of bovine
            casein block A"

(xi) SEQUENCE DESCRIPTION: SEQ ID NO:13:

Asn Gln Asp Pro Gly His Met Arg Pro Lys His Pro Ile Lys His Gln
 1               5                  10                  15

Gly Leu Pro Gln Glu Val Leu Asn Glu Asn Leu Leu Arg Tyr Tyr Val
             20                  25                  30

Ala Pro Tyr Pro Glu Val Tyr Gly Lys Glu Lys Val Asn Glu Leu Ser
         35                  40                  45

Lys Asp Ile Gly Ser Glu Ser Thr Glu Asp Gln Ala Met Glu Asp Ile
     50                  55                  60
```

```
Lys Gln Met Glu Ala Glu Ser Ile Ser Ser Glu Glu Ile Val Pro
 65                  70                  75                  80

Asn Ser Val Glu Gln Lys His Ile Gln Lys Glu Asp Val Pro Ser Glu
                 85                  90                  95

Arg Tyr Leu Gly Tyr Leu Glu Gln Leu Leu Arg Leu Lys Lys Tyr Lys
                100                 105                 110

Val Pro Gln Leu Glu Ile Val Pro Asn Ser Ala Glu Glu
                115                 120                 125
```

(2) INFORMATION FOR SEQ ID NO:14:

(i) SEQUENCE CHARACTERISTICS:
        (A) LENGTH: 371 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..371
        (D) OTHER INFORMATION: /note= "actual sequence obtained for
            bovine casein block A"

(xi) SEQUENCE DESCRIPTION: SEQ ID NO:14:

```
AATCAGGATC CCGGGCATAT GAGACCAAAA CATCCAATTA AACATCAAGG TTTGCCACAA    60

GAAGTTTTGA ACGAAAACTT GTTGAGATAC TACGTTGCTC CATACCCAGA AGTTTACGGT   120

AAAGAAAAAG TTAATGAATT GTCTAAAGAT ATCGGTTCTG AATCTACTGA AGATCAAGCC   180

ATGGAAGATA TTAAACAAAT GGAAGCTGAA TCTATCTCTT CTTCTGAAGA AATCGTCCCA   240

AACTCTGAAC AAAAACATAT TCAAAAAGAA GACGTCCCAT CTGAAAGATA CTTGGGTTAC   300

TTAGAACAAT TGTTGAGATT GAAAAAATAC AAAGTTCCAC AATTGGAAAT CGTCCCAAAC   360

TCAGCTGAAG A                                                        371
```

(2) INFORMATION FOR SEQ ID NO:15:

(i) SEQUENCE CHARACTERISTICS:
        (A) LENGTH: 124 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..124
        (D) OTHER INFORMATION: /note= "actual sequence obtained for
            bovine casein block A"

(xi) SEQUENCE DESCRIPTION: SEQ ID NO:15:

```
Asn Gln Asp Pro Gly His Met Arg Pro Lys His Pro Ile Lys His Gln
  1               5                  10                  15

Gly Leu Pro Gln Glu Val Leu Asn Glu Asn Leu Leu Arg Tyr Tyr Val
                 20                  25                  30

Ala Pro Tyr Pro Glu Val Tyr Gly Lys Glu Lys Val Asn Glu Leu Ser
                 35                  40                  45

Lys Asp Ile Gly Ser Glu Ser Thr Glu Asp Gln Ala Met Glu Asp Ile
 50                  55                  60

Lys Gln Met Glu Ala Glu Ser Ile Ser Ser Glu Glu Ile Val Pro
 65                  70                  75                  80
```

```
Asn Ser Glu Gln Lys His Ile Gln Lys Glu Asp Val Pro Ser Glu Arg
                85                  90                  95

Tyr Leu Gly Tyr Leu Glu Gln Leu Leu Arg Leu Lys Lys Tyr Lys Val
            100                 105                 110

Pro Gln Leu Glu Ile Val Pro Asn Ser Ala Glu Glu
        115                 120
```

(2) INFORMATION FOR SEQ ID NO:16:

(i) SEQUENCE CHARACTERISTICS:
        (A) LENGTH: 371 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..371
        (D) OTHER INFORMATION: /note= "predicted sequence of bovine
            casein block B"

(xi) SEQUENCE DESCRIPTION: SEQ ID NO:16:

```
CAAAAAGAAG ACGTCCCATC TGAAAGATAC TTGGGTTACT TAGAACAATT GTTGAGATTG      60

AAAAAATACA AAGTTCCACA ATTGGAAATC GTCCCAAACT CAGCTGAAGA AAGATTGCAT     120

TCTATGAAAG AAGGTATTCA TGCTCAACAA AAAGAACCAA TGATTGGTGT TAACCAAGAA     180

TTGGCTTACT ACTACCCAGA ATTGTACAGA CAATACTATC AATTGGATGC TTACCCATCT     240

GGTGCTTGGT ACTACGTTCC TTTAGGTACC CAATACACTG ATGCTCCATC TTACTCTGAT     300

ATTCCAAACC CAATCGGTTC TGAAAACTCT GAAAAAACTA CTATGCCATT GTGGTAATAA     360

GCTTCATGAT C                                                          371
```

(2) INFORMATION FOR SEQ ID NO:17:

(i) SEQUENCE CHARACTERISTICS:
        (A) LENGTH: 118 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..118
        (D) OTHER INFORMATION: /note= "predicted sequence of bovine
            casein block B"

(xi) SEQUENCE DESCRIPTION: SEQ ID NO:17:

```
Gln Lys Glu Asp Val Pro Ser Glu Arg Tyr Leu Gly Tyr Leu Glu Gln
1               5                   10                  15

Leu Leu Arg Leu Lys Lys Tyr Lys Val Pro Gln Leu Glu Ile Val Pro
            20                  25                  30

Asn Ser Ala Glu Glu Arg Leu His Ser Met Lys Glu Gly Ile His Ala
        35                  40                  45

Gln Gln Lys Glu Pro Met Ile Gly Val Asn Gln Glu Leu Ala Tyr Tyr
    50                  55                  60

Tyr Pro Glu Leu Tyr Arg Gln Tyr Tyr Gln Leu Asp Ala Tyr Pro Ser
65                  70                  75                  80

Gly Ala Trp Tyr Tyr Val Pro Leu Gly Thr Gln Tyr Thr Asp Ala Pro
            85                  90                  95

Ser Tyr Ser Asp Ile Pro Asn Pro Ile Gly Ser Glu Asn Ser Glu Lys
```

100             105             110
Thr Thr Met Pro Leu Trp
        115

(2) INFORMATION FOR SEQ ID NO:18:

(i) SEQUENCE CHARACTERISTICS:
        (A) LENGTH: 371 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..371
        (D) OTHER INFORMATION: /note= "actual sequence obtained for
            bovine casein block B"

(xi) SEQUENCE DESCRIPTION: SEQ ID NO:18:

CAAAAAGAAG ACGTCCCATC TGAAAGATAC TTGGGTTACT TAGAACAATT GTTGAGATTG      60

AAAAAATACA AAGTTCCACA ATTGGAAATC GTCCCAAACT CAGCTGAAGA AAGATTGCAT     120

TCTATGAAAA GAAGGTATTC ATGCTCAACA AAAAGAACCA ATGATTGGTG TTAACCAAGA     180

ATTGGCTTAC TACTACCCAG AATTGTACAG ACAATACTAT CAATTGATGC TTACCCATCT     240

GGTGCTTTGT ACTACGTTCC TTTAGGTACC CAATACACTG ATGCTCCATC TTACTCTGAT     300

ATTCCAAACC CAATCGGTTC TGAAAACTCT GAAAAAACTA CTATGCCATT GTGGTAATAA     360

GCTTCATGAT C                                                         371

(2) INFORMATION FOR SEQ ID NO:19:

(i) SEQUENCE CHARACTERISTICS:
        (A) LENGTH: 118 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..124
        (D) OTHER INFORMATION: /note= "actual sequence obtained for
            bovine casein block B"

(xi) SEQUENCE DESCRIPTION: SEQ ID NO:19:

Gln Lys Glu Asp Val Pro Ser Glu Arg Tyr Leu Gly Tyr Leu Glu Gln
1               5                   10                  15

Leu Leu Arg Leu Lys Lys Tyr Lys Val Pro Gln Leu Glu Ile Val Pro
            20                  25                  30

Asn Ser Ala Glu Glu Arg Leu His Ser Met Lys Glu Gly Ile His Ala
        35                  40                  45

Gln Gln Lys Glu Pro Met Ile Gly Val Asn Gln Glu Leu Ala Tyr Tyr
    50                  55                  60

Tyr Pro Glu Leu Tyr Arg Gln Tyr Tyr Gln Leu Asp Ala Tyr Pro Ser
65                  70                  75                  80

Gly Ala Leu Tyr Tyr Val Pro Leu Gly Thr Gln Tyr Thr Asp Ala Pro
                85                  90                  95

Ser Tyr Ser Asp Ile Pro Asn Pro Ile Gly Ser Glu Asn Ser Glu Lys
            100                 105                 110

Thr Thr Met Pro Leu Trp
        115

(2) INFORMATION FOR SEQ ID NO:20:

(i) SEQUENCE CHARACTERISTICS:
        (A) LENGTH: 632 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..632
        (D) OTHER INFORMATION: /note= "combined sequence of bovine
            casein blocks A and B"

(xi) SEQUENCE DESCRIPTION: SEQ ID NO:20:

```
AATCAGGATC CCGGGCATAT GAGACCAAAA CATCCAATTA AACATCAAGG TTTGCCACAA      60

GAAGTTTTGA ACGAAAACTT GTTGAGATAC TACGTTGCTC CATACCCAGA AGTTTACGGT     120

AAAGAAAAAG TTAATGAATT GTCTAAAGAT ATCGGTTCTG AATCTACTGA AGATCAAGCC     180

ATGGAAGATA TTAAACAAAT GGAAGCTGAA TCTATCTCTT CTTCTGAAGA AATCGTCCCA     240

AACTCTGAAC AAAAACATAT TCAAAAAGAA GACGTCCCAT CTGAAAGATA CTTGGGTTAC     300

TTAGAACAAT TGTTGAGATT GAAAAAATAC AAAGTTCCAC CATTGGAAAT CGTCCCAAAC     360

TCAGCTGAAG AAAGATTGCA TTCTATGAAA GAAGGTATTC ATGCTCAACA AAAAGAACCA     420

ATGATTGGTG TTAACCAAGA ATTGGCTTAC TACTACCCAG AATTGTACAG ACAATACTAT     480

CAATTGGATG CTTACCCATC TGGTGCTTTG TACTACGTTC CTTTAGGTAC CCAATACACT     540

GATGCTCCAT CTTACTCTGA TATTCCAAAC CCAATCGGTT CTGAAAACTC TGAAAAAACT     600

ACTATGCCAT TGTGGTAATA AGCTTCATGA TC                                   632
```

(2) INFORMATION FOR SEQ ID NO:21:

(i) SEQUENCE CHARACTERISTICS:
        (A) LENGTH: 200 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..200
        (D) OTHER INFORMATION: /note= "combined sequence of bovine
            casein blocks A and B"

(xi) SEQUENCE DESCRIPTION: SEQ ID NO:21:

```
Asn Gln Asp Pro Gly His Asn Arg Pro Lys His Pro Ile Lys His Gln
 1               5                  10                  15

Gly Leu Pro Gln Glu Val Leu Asn Glu Asn Leu Leu Arg Tyr Tyr Val
            20                  25                  30

Ala Pro Tyr Pro Glu Val Tyr Gly Lys Glu Lys Val Asn Glu Leu Ser
        35                  40                  45

Lys Asp Ile Gly Ser Glu Ser Thr Glu Asp Gln Ala Asn Glu Asp Ile
    50                  55                  60

Lys Gln Asn Glu Ala Glu Ser Ile Ser Ser Ser Glu Glu Ile Val Pro
65                  70                  75                  80

Asn Ser Glu Gln Lys His Ile Gln Lys Glu Asp Val Pro Ser Glu Arg
                85                  90                  95

Tyr Leu Gly Tyr Leu Glu Gln Leu Leu Arg Leu Lys Lys Tyr Lys Val
```

```
                  100              105              110
Pro Gln Leu Glu Ile Val Pro Asn Ser Ala Glu Glu Arg Leu His Ser
        115                  120                  125

Asn Lys Glu Gly Ile His Ala Gln Gln Lys Glu Pro Asn Ile Gly Val
    130                  135                  140

Asn Gln Glu Leu Ala Tyr Tyr Tyr Pro Glu Leu Tyr Arg Gln Tyr Tyr
145                  150                  155                  160

Gln Leu Asp Ala Tyr Pro Ser Gly Ala Leu Tyr Tyr Val Pro Leu Gly
                165                  170                  175

Thr Gln Tyr Thr Asp Ala Pro Ser Tyr Ser Asp Ile Pro Asn Pro Ile
            180                  185                  190

Gly Ser Glu Asn Ser Glu Lys Thr
        195                  200
```

(2) INFORMATION FOR SEQ ID NO:22:

(i) SEQUENCE CHARACTERISTICS:
        (A) LENGTH: 632 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..632
        (D) OTHER INFORMATION: /note= "final sequence of synthetic
            bovine casein gene"

(xi) SEQUENCE DESCRIPTION: SEQ ID NO:22:

```
AATCAGGATC CCGGGCTGCA GAGACCAAAA CATCCAATTA AACATCAAGG TTTGCCACAA    60
GAAGTTTTGA ACGAAAACTT GTTGAGATAC TACGTTGCTC ATACCCAGA AGTTTACGGT    120
AAAGAAAAAG TTAATGAATT GTCTAAAGAT ATCGGTTCTG AATCTACTGA AGATCAAGCC   180
ATGGAAGATA TTAAACAAAT GGAAGCTGAA TCTATCTCTT CTTCTGAAGA AATCGTCCCA   240
AACTCTGAAC AAAAACATAT TCAAAAAGAA GACGTCCCAT CTGAAAGATA CTTGGGTTAC   300
TTAGAACAAT TGTTGAGATT GAAAAAATAC AAAGTTCCAC AATTGGAAAT CGTCCCAAAC   360
TCAGCTGAAG AAAGATTGCA TTCTATGAAA GAAGGTATTC ATGCTCAACA AAAAGAACCA   420
ATGATTGGTG TTAACCACGA ATTGGCTTAC TACTACCCAG AATTGTACAG ACAATACTAT   480
CAATTGGATG CTTACCCATC TGGTGCTTTG TACTACGTTC CTTTAGGTAC CCAATACACT   540
GATGCTCCAT CTTACTCTGA TATTCCAAAC CCAATCGGTT CTGAAAACTC TGAAAAAACT   600
ACTATGCCAT TGTGGTAATA AGCTTCATGA TC                                 632
```

(2) INFORMATION FOR SEQ ID NO:23:

(i) SEQUENCE CHARACTERISTICS:
        (A) LENGTH: 200 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..200
        (D) OTHER INFORMATION: /note= "final sequence of synthetic
            bovine casein"

(xi) SEQUENCE DESCRIPTION: SEQ ID NO:23:

```
Asn Gln Asp Pro Gly His Asn Arg Pro Lys His Pro Ile Lys His Gln
1               5                   10                  15

Gly Leu Pro Gln Glu Val Leu Asn Glu Asn Leu Leu Arg Tyr Tyr Val
            20                  25                  30

Ala Pro Tyr Pro Glu Val Tyr Gly Lys Glu Lys Val Asn Glu Leu Ser
        35                  40                  45

Lys Asp Ile Gly Ser Glu Ser Thr Glu Asp Gln Ala Asn Glu Asp Ile
50                  55                  60

Lys Gln Asn Glu Ala Glu Ser Ile Ser Ser Glu Glu Ile Val Pro
65                  70                  75                  80

Asn Ser Glu Gln Lys His Ile Gln Lys Glu Asp Val Pro Ser Glu Arg
                85                  90                  95

Tyr Leu Gly Tyr Leu Glu Gln Leu Leu Arg Leu Lys Lys Tyr Lys Val
            100                 105                 110

Pro Gln Leu Glu Ile Val Pro Asn Ser Ala Glu Glu Arg Leu His Ser
            115                 120                 125

Asn Lys Glu Gly Ile His Ala Gln Gln Lys Glu Pro Asn Ile Gly Val
        130                 135                 140

Asn Gln Glu Leu Ala Tyr Tyr Pro Glu Leu Tyr Arg Gln Tyr Tyr
145                 150                 155                 160

Gln Leu Asp Ala Tyr Pro Ser Gly Ala Leu Tyr Tyr Val Pro Leu Gly
                165                 170                 175

Thr Gln Tyr Thr Asp Ala Pro Ser Tyr Ser Asp Ile Pro Asn Pro Ile
            180                 185                 190

Gly Ser Glu Asn Ser Glu Lys Thr
        195                 200

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

GATCCCGGGC TGCAGAGACC AAAAC                                         25

(2) INFORMATION FOR SEQ ID NO:25:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

GATCATGAAG CTTATTACCA CAATGG                                        26

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA
```

(ix) FEATURE:
             (A) NAME/KEY: -
             (B) LOCATION: 1..20
             (D) OTHER INFORMATION: /note "5'-terminal oligonucleotide PCR
                 primer for Block A"

(xi) SEQUENCE DESCRIPTION: SEQ ID NO:26:

AATCAGGATC CCGGGCATAT                                                      20

(2) INFORMATION FOR SEQ ID NO:27:

(i) SEQUENCE CHARACTERISTICS:
             (A) LENGTH: 103 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: -
             (B) LOCATION: 1..103
             (D) OTHER INFORMATION: /note= "casein 1"

(xi) SEQUENCE DESCRIPTION: SEQ ID NO:27:

AATCAGGATC CCGGGCATAT GAGACCAAAA CATCCAATTA AACATCAAGG TTTGCCACAA          60

GAAGTTTTGA ACGAAAACTT GTTGAGATAC TACGTTGCTC CAT                           103

(2) INFORMATION FOR SEQ ID NO:28:

(i) SEQUENCE CHARACTERISTICS:
             (A) LENGTH: 109 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: -
             (B) LOCATION: 1..109
             (D) OTHER INFORMATION: /note= "casein 2"

(xi) SEQUENCE DESCRIPTION: SEQ ID NO:28:

AATATCTTCC ATGGCTTGAT CTTCAGTAGA TTCAGAACCG ATATCTTTAG ACAATTCATT          60

AACTTTTTCT TTACCGTAAA CTTCTGGGTA TGGAGCAACG TAGTATCTC                     109

(2) INFORMATION FOR SEQ ID NO:29:

(i) SEQUENCE CHARACTERISTICS:
             (A) LENGTH: 112 base pairs
             (B) TYPE: nucleic acid
             (C) STRANDEDNESS: single
             (D) TOPOLOGY: linear (ii) MOLECULE TYPE: DNA (ix) FEATURE:
             (A) NAME/KEY: -
             (B) LOCATION: 1..112
             (D) OTHER INFORMATION: /note= "casein 3"

(xi) SEQUENCE DESCRIPTION: SEQ ID NO:29:

ATCAAGCCAT GGAAGATATT AAACAAATGG AAGCTGAATC TATCTCTTCT TCTGAAGAAA          60

TCGTCCCAAA CTCTGTTGAA CAAAAACATA TTCAAAAAGA AGACGTCCCA TC                 112

(2) INFORMATION FOR SEQ ID NO:30:

(i) SEQUENCE CHARACTERISTICS:
            (A) LENGTH: 110 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..110
            (D) OTHER INFORMATION: /note= "casein 4"

(xi) SEQUENCE DESCRIPTION: SEQ ID NO:30:

TCTTCAGCTG AGTTTGGGAC GATTTCCAAT TGTGGAACTT TGTATTTTTT CAATCTCAAC         60

AATTGTTCTA AGTAACCCAA GTATCTTTCA GATGGGACGT CTTCTTTTTG                  110

(2) INFORMATION FOR SEQ ID NO:31:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..20
            (D) OTHER INFORMATION: /note "3'-terminal oligonucleotide PCR
                primer for Block A"

(xi) SEQUENCE DESCRIPTION: SEQ ID NO:31:

TCTTCAGCTG AGTTTGGGAC                                                    20

(2) INFORMATION FOR SEQ ID NO:32:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..20
            (D) OTHER INFORMATION: /note "5'-terminal oligonucleotide PCR
                primer for Block B"

(xi) SEQUENCE DESCRIPTION: SEQ ID NO:32:

CAAAAAGAAG ACGTCCCATC                                                    20

(2) INFORMATION FOR SEQ ID NO:33:

(i) SEQUENCE CHARACTERISTICS:
            (A) LENGTH: 110 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: -
            (B) LOCATION: 1..110
            (D) OTHER INFORMATION: /note= "casein 5"

(xi) SEQUENCE DESCRIPTION: SEQ ID NO:33:

CAAAAAGAAG ACGTCCCATC TGAAAGATAC TTGGGTTACT TAGAACAATT GTTGAGATTG    60

AAAAAATACA AAGTTCCACA ATTGGAAATC GTCCCAAACT CAGCTGAAGA           110

(2) INFORMATION FOR SEQ ID NO:34:

(i) SEQUENCE CHARACTERISTICS:
        (A) LENGTH: 110 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..110
        (D) OTHER INFORMATION: /note= "casein 6"

(xi) SEQUENCE DESCRIPTION: SEQ ID NO:34:

TCTGGGTAGT AGTAAGCCAA TTCTTGGTTA ACACCAATCA TTGGTTCTTT TTGTTGAGCA    60

TGAATACCTT CTTTCATAGA ATGCAATCTT TCTTCAGCTG AGTTTGGAAC           110

(2) INFORMATION FOR SEQ ID NO:35:

(i) SEQUENCE CHARACTERISTICS:
        (A) LENGTH: 100 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..100
        (D) OTHER INFORMATION: /note= "casein 7"

(xi) SEQUENCE DESCRIPTION: SEQ ID NO:35:

TTGGCTTACT ACTACCCAGA ATTGTACAGA CAATACTATC AATTGGATGC TTACCCATCT    60

GGTGCTTGGT ACTACGTTCC TTTAGGTACC CAATACACTG                    100

(2) INFORMATION FOR SEQ ID NO:36:

(i) SEQUENCE CHARACTERISTICS:
        (A) LENGTH: 116 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..116
        (D) OTHER INFORMATION: /note= "casein 8"

(xi) SEQUENCE DESCRIPTION: SEQ ID NO:36:

GACTTGATCA TGAAGCTTAT TACCACAATG GCATAGTAGT TTTTTCAGAG TTTTCAGAAC    60

CGATTGGGTT TGGAATATCA GAGTAAGATG GAGCATCAGT GTATTGGGTA CCTAAA    116

(2) INFORMATION FOR SEQ ID NO:37:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (ix) FEATURE:
            (A) NAME/KEY: -
            (B) LOCATION: 1..61
            (D) OTHER INFORMATION: /note "3'-terminal oligonucleotide PCR
                primer for Block B"

(xi) SEQUENCE DESCRIPTION: SEQ ID NO:37:

```
GATCATGAAG CTTATTACCA CAATGGCATA GTAGTTTTTT CAGAGTTTTC AGAACCGATT      60

G                                                                      61
```

(2) INFORMATION FOR SEQ ID NO:38:

(i) SEQUENCE CHARACTERISTICS:
            (A) LENGTH: 1873 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Gallus gallus (ix) FEATURE:
            (A) NAME/KEY: -
            (B) LOCATION: 1..1873
            (D) OTHER INFORMATION: /note= "chicken ovalbumin mRNA"

(ix) FEATURE:
            (A) NAME/KEY: CDS
            (B) LOCATION: 66..1226
            (D) OTHER INFORMATION: /product= "Ovalbumin, Chicken"

(xi) SEQUENCE DESCRIPTION: SEQ ID NO:38:

```
GACATACAGC TAGAAAGCTG TATTGCCTTT AGCACTCAAG CTCAAAAGAC AACTCAGAGT       60

TCACC ATG GGC TCC ATC GGC GCA GCA AGC ATG GAA TTT TGT TTT GAT         107
      Met Gly Ser Ile Gly Ala Ala Ser Met Glu Phe Cys Phe Asp
        1               5                  10

GTA TTC AAG GAG CTC AAA GTC CAC CAT GCC AAT GAG AAC ATC TTC TAC       155
Val Phe Lys Glu Leu Lys Val His His Ala Asn Glu Asn Ile Phe Tyr
 15              20                  25                  30

TGC CCC ATT GCC ATC ATG TCA GCT CTA GCC ATG GTA TAC CTG GGT GCA       203
Cys Pro Ile Ala Ile Met Ser Ala Leu Ala Met Val Tyr Leu Gly Ala
                 35                  40                  45

AAA GAC AGC ACC AGG ACA CAG ATA AAT AAG GTT GTT CGC TTT GAT AAA       251
Lys Asp Ser Thr Arg Thr Gln Ile Asn Lys Val Val Arg Phe Asp Lys
             50                  55                  60

CTT CCA GGA TTC GGA GAC AGT ATT GAA GCT CAG TGT GGC ACA TCT GTA       299
Leu Pro Gly Phe Gly Asp Ser Ile Glu Ala Gln Cys Gly Thr Ser Val
         65                  70                  75

AAC GTT CAC TCT TCA CTT AGA GAC ATC CTC AAC CAA ATC ACC AAA CCA       347
Asn Val His Ser Ser Leu Arg Asp Ile Leu Asn Gln Ile Thr Lys Pro
     80                  85                  90

AAT GAT GTT TAT TCG TTC AGC CTT GCC AGT AGA CTT TAT GCT GAA GAG       395
Asn Asp Val Tyr Ser Phe Ser Leu Ala Ser Arg Leu Tyr Ala Glu Glu
 95                 100                 105                 110

AGA TAC CCA ATC CTG CCA GAA TAC TTG CAG TGT GTG AAG GAA CTG TAT       443
Arg Tyr Pro Ile Leu Pro Glu Tyr Leu Gln Cys Val Lys Glu Leu Tyr
                115                 120                 125

AGA GGA GGC TTG GAA CCT ATC AAC TTT CAA ACA GCT GCA GAT CAA GCC       491
Arg Gly Gly Leu Glu Pro Ile Asn Phe Gln Thr Ala Ala Asp Gln Ala
            130                 135                 140
```

```
AGA GAG CTC ATC AAT TCC TGG GTA GAA AGT CAG ACA AAT GGA ATT ATC        539
Arg Glu Leu Ile Asn Ser Trp Val Glu Ser Gln Thr Asn Gly Ile Ile
        145                 150                 155

AGA AAT GTC CTT CAG CCA AGC TCC GTG GAT TCT CAA ACT GCA ATG GTT        587
Arg Asn Val Leu Gln Pro Ser Ser Val Asp Ser Gln Thr Ala Met Val
    160                 165                 170

CTG GTT AAT GCC ATT GTC TTC AAA GGA CTG TGG GAG AAA ACA TTT AAG        635
Leu Val Asn Ala Ile Val Phe Lys Gly Leu Trp Glu Lys Thr Phe Lys
175                 180                 185                 190

GAT GAA GAC ACA CAA GCA ATG CCT TTC AGA GTG ACT GAG CAA GAA AGC        683
Asp Glu Asp Thr Gln Ala Met Pro Phe Arg Val Thr Glu Gln Glu Ser
                195                 200                 205

AAA CCT GTG CAG ATG ATG TAC CAG ATT GGT TTA TTT AGA GTG GCA TCA        731
Lys Pro Val Gln Met Met Tyr Gln Ile Gly Leu Phe Arg Val Ala Ser
            210                 215                 220

ATG GCT TCT GAG AAA ATG AAG ATC CTG GAG CTT CCA TTT GCC AGT GGG        779
Met Ala Ser Glu Lys Met Lys Ile Leu Glu Leu Pro Phe Ala Ser Gly
        225                 230                 235

ACA ATG AGC ATG TTG GTG CTG TTG CCT GAT GAA GTC TCA GGC CTT GAG        827
Thr Met Ser Met Leu Val Leu Leu Pro Asp Glu Val Ser Gly Leu Glu
    240                 245                 250

CAG CTT GAG AGT ATA ATC AAC TTT GAA AAA CTG ACT GAA TGG ACC AGT        875
Gln Leu Glu Ser Ile Ile Asn Phe Glu Lys Leu Thr Glu Trp Thr Ser
255                 260                 265                 270

TCT AAT GTT ATG GAA GAG AGG AAG ATC AAA GTG TAC TTA CCT CGC ATG        923
Ser Asn Val Met Glu Glu Arg Lys Ile Lys Val Tyr Leu Pro Arg Met
                275                 280                 285

AAG ATG GAG GAA AAA TAC AAC CTC ACA TCT GTC TTA ATG GCT ATG GGC        971
Lys Met Glu Glu Lys Tyr Asn Leu Thr Ser Val Leu Met Ala Met Gly
            290                 295                 300

ATT ACT GAC GTG TTT AGC TCT TCA GCC AAT CTG TCT GGC ATC TCC TCA       1019
Ile Thr Asp Val Phe Ser Ser Ser Ala Asn Leu Ser Gly Ile Ser Ser
        305                 310                 315

GCA GAG AGC CTG AAG ATA TCT CAA GCT GTC CAT GCA GCA CAT GCA GAA       1067
Ala Glu Ser Leu Lys Ile Ser Gln Ala Val His Ala Ala His Ala Glu
    320                 325                 330

ATC AAT GAA GCA GGC AGA GAG GTG GTA GGG TCA GCA GAG GCT GGA GTG       1115
Ile Asn Glu Ala Gly Arg Glu Val Val Gly Ser Ala Glu Ala Gly Val
335                 340                 345                 350

GAT GCT GCA AGC GTC TCT GAA GAA TTT AGG GCT GAC CAT CCA TTC CTC       1163
Asp Ala Ala Ser Val Ser Glu Glu Phe Arg Ala Asp His Pro Phe Leu
                355                 360                 365

TTC TGT ATC AAG CAC ATC GCA ACC AAC GCC GTT CTC TTC TTT GGC AGA       1211
Phe Cys Ile Lys His Ile Ala Thr Asn Ala Val Leu Phe Phe Gly Arg
            370                 375                 380

TGT GTT TCC CCT TAAAAAGAAG AAAGCTGAAA AACTCTGTCC CTTCCAACAA           1263
Cys Val Ser Pro
            385

GACCCAGAGC ACTGTAGTAT CAGGGGTAAA ATGAAAAGTA TGTTCTCTGC TGCATCCAGA     1323

CTTCATAAAA GCTGGAGCTT AATCTAGAAA AAAAATCAGA AAGAAATTAC ACTGTGAGAA     1383

CAGGTGCAAT TCACTTTTCC TTTACACAGA GTAATACTGG TAACTCATGG ATGAAGGCTT     1443

AAGGGAATGA AATTGGACTC ACAGTACTGA GTCATCACAC TGAAAAATGC AACCTGATAC     1503

ATCAGCAGAA GGTTTATGGG GGAAAAATGC AGCCTTCCAA TTAAGCCAGA TATCTGTATG     1563

ACCAAGCTGC TCCAGAATTA GTCACTCAAA ATCTCTCAGA TTAAATTATC AACTGTCACC     1623

AACCATTCCT ATGCTGACAA GGCAATTGCT TGTTCTCTGT GTTCCTGATA CTACAAGGCT     1683

CTTCCTGACT TCCTAAAGAT GCATTATAAA AATCTTATAA TTCACATTTC TCCCTAAACT     1743
```

```
TTGACTCAAT CATGGTATGT TGGCAAATAT GGTATATTAC TATTCAAATT GTTTTCCTTG    1803

TACCCATATG TAATGGGTCT TGTGAATGTG CTCTTTTGTT CCTTTAATCA TAATAAAAAC    1863

ATGTTTAAGC                                                           1873
```

(2) INFORMATION FOR SEQ ID NO:39:

(i) SEQUENCE CHARACTERISTICS:
        (A) LENGTH: 386 amino acids
        (B) TYPE: amino acid
        (D) TOPOLOGY: linear (ii) MOLECULE TYPE: protein (xi) SEQUENCE DESCRIPTION: SEQ ID NO:39:

```
Met Gly Ser Ile Gly Ala Ala Ser Met Glu Phe Cys Phe Asp Val Phe
 1               5                  10                  15

Lys Glu Leu Lys Val His His Ala Asn Glu Asn Ile Phe Tyr Cys Pro
                20                  25                  30

Ile Ala Ile Met Ser Ala Leu Ala Met Val Tyr Leu Gly Ala Lys Asp
            35                  40                  45

Ser Thr Arg Thr Gln Ile Asn Lys Val Val Arg Phe Asp Lys Leu Pro
    50                  55                  60

Gly Phe Gly Asp Ser Ile Glu Ala Gln Cys Gly Thr Ser Val Asn Val
65                  70                  75                  80

His Ser Ser Leu Arg Asp Ile Leu Asn Gln Ile Thr Lys Pro Asn Asp
                85                  90                  95

Val Tyr Ser Phe Ser Leu Ala Ser Arg Leu Tyr Ala Glu Glu Arg Tyr
            100                 105                 110

Pro Ile Leu Pro Glu Tyr Leu Gln Cys Val Lys Glu Leu Tyr Arg Gly
    115                 120                 125

Gly Leu Glu Pro Ile Asn Phe Gln Thr Ala Ala Asp Gln Ala Arg Glu
130                 135                 140

Leu Ile Asn Ser Trp Val Glu Ser Gln Thr Asn Gly Ile Ile Arg Asn
145                 150                 155                 160

Val Leu Gln Pro Ser Ser Val Asp Ser Gln Thr Ala Met Val Leu Val
                165                 170                 175

Asn Ala Ile Val Phe Lys Gly Leu Trp Glu Lys Thr Phe Lys Asp Glu
            180                 185                 190

Asp Thr Gln Ala Met Pro Phe Arg Val Thr Glu Gln Glu Ser Lys Pro
    195                 200                 205

Val Gln Met Met Tyr Gln Ile Gly Leu Phe Arg Val Ala Ser Met Ala
210                 215                 220

Ser Glu Lys Met Lys Ile Leu Glu Leu Pro Phe Ala Ser Gly Thr Met
225                 230                 235                 240

Ser Met Leu Val Leu Leu Pro Asp Glu Val Ser Gly Leu Glu Gln Leu
                245                 250                 255

Glu Ser Ile Ile Asn Phe Glu Lys Leu Thr Glu Trp Thr Ser Ser Asn
            260                 265                 270

Val Met Glu Glu Arg Lys Ile Lys Val Tyr Leu Pro Arg Met Lys Met
    275                 280                 285

Glu Glu Lys Tyr Asn Leu Thr Ser Val Leu Met Ala Met Gly Ile Thr
290                 295                 300

Asp Val Phe Ser Ser Ser Ala Asn Leu Ser Gly Ile Ser Ser Ala Glu
305                 310                 315                 320
```

```
Ser Leu Lys Ile Ser Gln Ala Val His Ala His Ala Glu Ile Asn
            325                 330                 335

Glu Ala Gly Arg Glu Val Val Gly Ser Ala Glu Ala Gly Val Asp Ala
            340                 345                 350

Ala Ser Val Ser Glu Glu Phe Arg Ala Asp His Pro Phe Leu Phe Cys
            355                 360                 365

Ile Lys His Ile Ala Thr Asn Ala Val Leu Phe Phe Gly Arg Cys Val
    370                 375                 380

Ser Pro
385
```

(2) INFORMATION FOR SEQ ID NO:40:

(i) SEQUENCE CHARACTERISTICS:
        (A) LENGTH: 1123 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Bos taurus (ix) FEATURE:
        (A) NAME/KEY: -
        (B) LOCATION: 1..1123
        (D) OTHER INFORMATION: /note= "bovine alpha-s1-casein mRNA"

(ix) FEATURE:
        (A) NAME/KEY: sig_peptide
        (B) LOCATION: 64..108
        (D) OTHER INFORMATION: /note= "bovine alpha-s1-casein signal
            peptide"

(ix) FEATURE:
        (A) NAME/KEY: mat_peptide
        (B) LOCATION: 109..705
        (D) OTHER INFORMATION: /note= "bovine alpha-s1-casein"

(ix) FEATURE:
        (A) NAME/KEY: CDS
        (B) LOCATION: 64..708
        (D) OTHER INFORMATION: /note= "bovine alpha-s1-casein
            precursor"

(xi) SEQUENCE DESCRIPTION: SEQ ID NO:40:

```
TCACTTCGAC CATCAACCCA GCTTGCTGTT CTTCCCAGTC TTGGGTTCAA GATCTTGACA      60

ACC ATG AAA CTT CTC ATC CTT ACC TGT CTT GTG GCT GTT GCT CTT GCC      108
    Met Lys Leu Leu Ile Leu Thr Cys Leu Val Ala Val Ala Leu Ala
    -15             -10                 -5

AGG CCC AAA CAT CCT ATC AAG CAC CAA GGA CTC CCT CAA GAA GTC CTC      156
Arg Pro Lys His Pro Ile Lys His Gln Gly Leu Pro Gln Glu Val Leu
  1               5                  10                  15

AAT GAA AAT TTA CTC AGG TTT TTT GTG GCA CCT TTT CCA GAA GTG TTT      204
Asn Glu Asn Leu Leu Arg Phe Phe Val Ala Pro Phe Pro Glu Val Phe
              20                  25                  30

GGA AAG GAG AAG GTC AAT GAA CTG AGC AAG GAT ATT GGG AGT GAA TCA      252
Gly Lys Glu Lys Val Asn Glu Leu Ser Lys Asp Ile Gly Ser Glu Ser
          35                  40                  45

ACT GAG GAT CAA GCC ATG GAA GAT ATT AAG CAA ATG GAA GCT GAA AGC      300
Thr Glu Asp Gln Ala Met Glu Asp Ile Lys Gln Met Glu Ala Glu Ser
      50                  55                  60

ATT TCG TCA AGT GAG GAA ATT GTT CCC AAT AGT GTT GAG CAG AAG CAC      348
Ile Ser Ser Ser Glu Glu Ile Val Pro Asn Ser Val Glu Gln Lys His
 65                  70                  75                  80
```

-continued

```
ATT CAA AAG GAA GAT GTG CCC TCT GAG CGT TAC CTG GGT TAT CTG GAA      396
Ile Gln Lys Glu Asp Val Pro Ser Glu Arg Tyr Leu Gly Tyr Leu Glu
                85                  90                  95

CAG CTT CTC AGA CTG AAA AAA TAC AAA GTA CCC CAG CTG GAA ATT GTT      444
Gln Leu Leu Arg Leu Lys Lys Tyr Lys Val Pro Gln Leu Glu Ile Val
            100                 105                 110

CCC AAT AGT GCT GAG GAA CGA CTT CAC AGT ATG AAA GAG GGA ATC CAT      492
Pro Asn Ser Ala Glu Glu Arg Leu His Ser Met Lys Glu Gly Ile His
        115                 120                 125

GCC CAA CAG AAA GAA CCT ATG ATA GGA GTG AAT CAG GAA CTG GCC TAC      540
Ala Gln Gln Lys Glu Pro Met Ile Gly Val Asn Gln Glu Leu Ala Tyr
    130                 135                 140

TTC TAC CCT GAG CTT TTC AGA CAA TTC TAC CAG CTG GAT GCC TAT CCA      588
Phe Tyr Pro Glu Leu Phe Arg Gln Phe Tyr Gln Leu Asp Ala Tyr Pro
145                 150                 155                 160

TCT GGT GCT TGG TAT TAC GTT CCA CTA GGC ACA CAA TAC ACT GAT GCC      636
Ser Gly Ala Trp Tyr Tyr Val Pro Leu Gly Thr Gln Tyr Thr Asp Ala
                165                 170                 175

CCA TCA TTC TCT GAC ATC CCT AAT CCC ATT GGC TCT GAG AAC AGT GAA      684
Pro Ser Phe Ser Asp Ile Pro Asn Pro Ile Gly Ser Glu Asn Ser Glu
            180                 185                 190

AAG ACT ACT ATG CCA CTG TGG TGAAGAGTCA AGTGAATTCT GAGGGACTCC         735
Lys Thr Thr Met Pro Leu Trp
        195

ACAGTTATGG TCTTTGATGG GTCTGAAAAT TCCATGCTCT ACATGTCGCC TCATCTACAT    795

GTCAAACCAT TCATCCAAAG GCTTCAACTG CTGTTTTAGA ACAGGGCAAT CTCAAACTGA    855

GGCACTCCTT GATGCTCTAC TGTATTTTAG ATAGTGTAAC ATCCTTAAGT GAAATTGTCC    915

TAACAGCTTG TTACCTAAAT TCCAGTAGTA TCATGCTGGT ATAAAGGCCA CTGAGTCAAA    975

GGGAATTAAA GTCTTCATTA AATTTCTGTA TGGAAAATGT TTTAAAGCC TTTGAATCAC    1035

TTCTCCTGTA AGTGCCATCA TATCAAATAA TTGTGTGCAT AACTGAGAT TTTGTCTTTC    1095

TTCTTTTCAA TAAATTACAT TTTAAGGC                                      1123
```

(2) INFORMATION FOR SEQ ID NO:41:

(i) SEQUENCE CHARACTERISTICS:
        (A) LENGTH: 214 amino acids
        (B) TYPE: amino acid
        (D) TOPOLOGY: linear (ii) MOLECULE TYPE: protein (xi) SEQUENCE DESCRIPTION: SEQ ID NO:41:

```
Met Lys Leu Leu Ile Leu Thr Cys Leu Val Ala Val Ala Leu Ala Arg
-15                 -10                 -5                    1

Pro Lys His Pro Ile Lys His Gln Gly Leu Pro Gln Glu Val Leu Asn
            5                   10                  15

Glu Asn Leu Leu Arg Phe Phe Val Ala Pro Phe Pro Glu Val Phe Gly
        20                  25                  30

Lys Glu Lys Val Asn Glu Leu Ser Lys Asp Ile Gly Ser Glu Ser Thr
    35                  40                  45

Glu Asp Gln Ala Met Glu Asp Ile Lys Gln Met Glu Ala Glu Ser Ile
50                  55                  60                  65

Ser Ser Ser Glu Glu Ile Val Pro Asn Ser Val Glu Gln Lys His Ile
                70                  75                  80

Gln Lys Glu Asp Val Pro Ser Glu Arg Tyr Leu Gly Tyr Leu Glu Gln
            85                  90                  95
```

```
Leu Leu Arg Leu Lys Lys Tyr Lys Val Pro Gln Leu Glu Ile Val Pro
            100                 105                 110

Asn Ser Ala Glu Glu Arg Leu His Ser Met Lys Glu Gly Ile His Ala
        115                 120                 125

Gln Lys Glu Pro Met Ile Gly Val Asn Gln Glu Leu Ala Tyr Phe
130             135                 140                 145

Tyr Pro Glu Leu Phe Arg Gln Phe Tyr Gln Leu Asp Ala Tyr Pro Ser
                150                 155                 160

Gly Ala Trp Tyr Tyr Val Pro Leu Gly Thr Gln Tyr Thr Asp Ala Pro
            165                 170                 175

Ser Phe Ser Asp Ile Pro Asn Pro Ile Gly Ser Glu Asn Ser Glu Lys
        180                 185                 190

Thr Thr Met Pro Leu Trp
    195
```

(2) INFORMATION FOR SEQ ID NO:42:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: -
        (B) LOCATION: 1..26
        (D) OTHER INFORMATION: /note= "mature bovine alpha-s1-casein"

(xi) SEQUENCE DESCRIPTION: SEQ ID NO:42:

```
Arg Pro Lys His Pro Ile Lys His Gln Gly Leu Pro Gln Glu Val Leu
1               5                   10                  15

Asn Glu Asn Leu Leu Arg Phe Phe Val Ala Pro Phe Pro Glu Val Phe
            20                  25                  30

Gly Lys Glu Lys Val Asn Glu Leu Ser Lys Asp Ile Gly Ser Glu Ser
        35                  40                  45

Thr Glu Asp Gln Ala Met Glu Asp Ile Lys Gln Met Glu Ala Glu Ser
50              55                  60

Ile Ser Ser Ser Glu Glu Ile Val Pro Asn Ser Val Glu Gln Lys His
65                  70                  75                  80

Ile Gln Lys Glu Asp Val Pro Ser Glu Arg Tyr Leu Gly Tyr Leu Glu
            85                  90                  95

Gln Leu Leu Arg Leu Lys Lys Tyr Lys Val Pro Gln Leu Glu Ile Val
            100                 105                 110

Pro Asn Ser Ala Glu Glu Arg Leu His Ser Met Lys Glu Gly Ile His
        115                 120                 125

Ala Gln Gln Lys Glu Pro Met Ile Gly Val Asn Gln Glu Leu Ala Tyr
    130                 135                 140

Phe Tyr Pro Glu Leu Phe Arg Gln Phe Tyr Gln Leu Asp Ala Tyr Pro
145                 150                 155                 160

Ser Gly Ala Trp Tyr Tyr Val Pro Leu Gly Thr Gln Tyr Thr Asp Ala
                165                 170                 175

Pro Ser Phe Ser Asp Ile Pro Asn Pro Ile Gly Ser Glu Asn Ser Glu
            180                 185                 190

Lys Thr Thr Met Pro Leu Trp
    195
```

```
(2) INFORMATION FOR SEQ ID NO:43:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..26
        (D) OTHER INFORMATION: /note= "polylinker containing
            restriction sites for PstI, BamHI, SmaI,
            EcoRI and HindIII"

(xi) SEQUENCE DESCRIPTION: SEQ ID NO:43:

CTGCAGGATC CCGGGAATTC AAGCTT                                              26
```

What is claimed is:

1. An isolated DNA molecule coding for a food protein, wherein the DNA is modified in that codons coding for all phenylalanines are omitted or replaced by codons coding for one or more other amino acids.

2. A food protein modified in that phenylalanine residues are omitted or replaced by one or more other amino acids.

3. A nutrient material comprising a modified food protein as defined in claim 2 and other edible substances.

4. A DNA molecule according to claim 1 wherein codons for phenylalanine are replaced by codons for tyrosine.

5. A nutrient material according to claim 2 wherein the modified food protein is in purified form.

6. An expression vector comprising a DNA molecule according to either of claims 1 or 4.

7. A DNA molecule according to claim 1 or 4, wherein the food protein is ovalbumin or casein.

8. A food protein according to claim 2, wherein the food protein is ovalbumin or casein.

9. An isolated host cell transformed by an expression vector according to claim 6.

10. A host cell according to claim 9, which is a yeast.

11. A host cell according to claim 10, which is *S. cerevisiae* or *Pichia pastoris*.

12. A method of producing a modified food protein according to claim 2 comprising transforming a host cell with an expression vector comprising a DNA molecule coding for the modified food protein, culturing the transformed host, and recovering the modified food protein.

13. A method according to claim 12, wherein the modified protein is partially purified from phenylalanine-containing proteins from the host cell forming a composition comprising the modified food protein and the phenylalanine containing proteins in appropriate proportions to supply the metabolic requirements without excess of phenylalanine to a phenylketonuria patient.

14. A nutrient material comprising the partially-purified modified protein and phenylalanine-containing proteins obtained by the method of claim 13.

15. A method of treating phenylketonuria in a patient, comprising administering to the patient a food protein modified in that codons coding for all phenylalanines are omitted or replaced by codons coding for one or more other amino acids.

* * * * *